United States Patent [19]

Goodman et al.

[11] 4,363,877

[45] Dec. 14, 1982

[54] RECOMBINANT DNA TRANSFER VECTORS

[75] Inventors: Howard M. Goodman; John Shine; Peter H. Seeburg, all of San Francisco, Calif.

[73] Assignee: The Regents of the University of California, Berkeley, Calif.

[21] Appl. No.: 897,710

[22] Filed: Apr. 19, 1978

Related U.S. Application Data

[63] Continuation-in-part of Ser. No. 836,218, Sep. 23, 1977, abandoned.

[51] Int. Cl.[3] .............................................. C12N 1/00

[52] U.S. Cl. .................................. 435/317; 435/172; 435/68; 435/91; 435/849

[58] Field of Search .................. 435/172, 317, 820, 68

[56] References Cited

PUBLICATIONS

Seeburg et al., Nature 270, 486–494, (1977).

Shine et al., Nature, 294–299, (1977).

Rodriguez et al., ICN-UCLA Symposium on Molecular and Genetic Biology Academic Press, (1976).

Tashjian et al., Endochrinology 82, 342–352, (1968).

Wallis et al., Growth Hormone and Related Peptides Ed Copecile et al., Elsevier, pp. 1–13, (1976).

Seeburg et al., Cell 12, 157–165, (1977).

Dayhoff, Atlas of Protein Sequence and Structure 5, Suppl. 2, pp. 120–121, Wash., D.C. 1976.

Martial et al., Proc. Nat. Acad. Science U.S.A. 74, 1816–1820, (1977).

Niall et al., Proc. Nat. Acad. Science, U.S.A. 68, 866–869, (1971).

Roberts et al., Proc. Nat. Acad. Science U.S.A. 70, 2330–2334, (1973).

Scheller et al., Science 196, 177–180, Apr. 1977.

Efstratiadis et al., Genetic Engineering, pp. 15–36, Edited by Setlow et al., Penum Press, New York, 1979.

Braverman, Methods in Enzymology, vol. XXX, Part F, pp. 605–612, (1974).

Bancroft et al., Proc. Nat. Acad. Sci. U.S.A. 70, 3646–3649, (1973).

Ullrich et al., Science, vol. 196, pp. 1313–1319, Jun. 17, 1977.

Szostak et al., Methods in Enzymology, vol. 68, Recombinant DNA, pp. 419–428, (1979).

*Primary Examiner*—Alvin E. Tanenholtz
*Attorney, Agent, or Firm*—Keil & Witherspoon

[57] ABSTRACT

Recombinant DNA transfer vectors containing codons for human somatomammotropin and for human growth hormone.

8 Claims, 5 Drawing Figures

RECOMBINANT DNA TRANSFER VECTORS

The Government has rights in this invention pursuant to Grants No. AM-18878 and CA 14026 awarded by the Department of Health, Education and Welfare.

This application in a continuation-in-part of copending application, Ser. No. 836,218, filed Sept. 23, 1977 and now abandoned.

BACKGROUND OF THE INVENTION

Proteins and peptides are synthesized in almost endless variety by living organisms. Many have proven to have medical, agricultural or industrial utility. Some proteins are enzymes, useful as specific catalysts for complex chemical reactions. Others function as hormones, which act to affect the growth or development of an organism or to affect the function of specific tissues in medically significant ways. Specific binding proteins may have commercial significance for the isolation and purification of trace substances and for the removal of contaminating substances. Both proteins and peptides are composed of linear chains of amino acids, the latter term being applied to short, single-chain sequences, the former referring to long-chain and multichain substances. The principles of the present invention apply equally to both proteins and peptides.

Proteins and peptides are generally high molecular weight substances, each having a specific sequence of amino acids. Except for the smaller peptides, chemical synthesis of peptides and proteins is frequently impractical, costly and time consuming, if not impossible. In the majority of instances, in order to make practical use of a desired protein, it must first be isolated from the organism which makes it. Frequently, the desired protein is present only in minuscule amounts. Often, the source organism cannot be obtained in quantities sufficient to provide an adequate amount of the desired protein. Consequently, many potential agricultural, industrial and medical applications for specific proteins are known, but remain undeveloped simply because an adequate supply of the desired protein or peptide does not exist.

Recently developed techniques have made it possible to employ microorganisms, capable of rapid and abundant growth, for the synthesis of commercially useful proteins and peptides, regardless of their source in nature. These techniques make it possible to genetically endow a suitable microorganism with the ability to synthesize a protein or peptide normally made by another organism. The technique makes use of a fundamental relationship which exists in all living organisms between the genetic material, usually DNA, and the proteins synthesized by the organism. This relationship is such that the amino acid sequence of the protein is reflected in the nucleotide sequence of the DNA. There are one or more trinucleotide sequence groups specifically related to each of the twenty amino acids most commonly occuring in proteins. The specific relationship between each given trinucleotide sequence and its corresponding amino acid constitutes the genetic code. The genetic code is believed to be the same or similar for all living organisms. As a consequence, the amino acid sequence of every protein or peptide is reflected by a corresponding nucleotide sequence, according to a well understood relationship. Furthermore, this sequence of nucleotides can, in principle, be translated by any living organism.

TABLE 1

Genetic Code

| | | | |
|---|---|---|---|
| Phenylalanine(Phe) | TTK | Histidine(HIS) | CAK |
| Leucine(Leu) | XTY | Glutamine(Gln) | CAJ |
| Isoleucine(Ile) | ATM | Asparagine(Asn) | AAK |
| Methionine(Met) | ATG | Lysine(Lys) | AAJ |
| Valine(Val) | GTL | Aspartic acid(AsP) | GAK |
| Serine(Ser) | QRS | Glutamic acid(Glu) | GAJ |
| Proline(Pro) | CCL | Cysteine(Cys) | TGK |
| Threonine(Thr) | ACL | Tryptophan(Tyr) | TGG |
| Alanine(Ala) | GCL | Arginine(Arg) | WGZ |
| Tyrosine(Tyr) | TAK | Glycine(Gly) | GGL |
| Termination signal | TAJ | | |
| Termination signal | TGA | | |

Key: Each 3-letter triplet represents a trinucleotide of DNA having a 5' end on the left and a 3' end on the right. The letters stand for the purine or pyrimidine bases forming the nucleotide sequence.

A = adenine
G = guanine
C = cytosine
J = A or G
K = T or C
L = A, T, C or G
M = A, C or T
T = thymine
X = T or C if Y is A or G
X = C if Y is C or T
Y = A, G, C or T if X is C
Y = A or G if X is T
W = C or A if Z is C or T
W = C if Z is C or T
Z = A, G, C or T if W is G
Z = A or G if W is A
QR = TC if S is A, G, C or T
QR = AG if S is T or C
S = A, G, C or T if QR is TC
S = T or C if QR is AG The trinucleotides of Table 1, termed codons, are presented as DNA trinucleotides, as they exist in the genetic material of a living organism. Expression of these codons in protein synthesis requires that intermediate formation of messenger RNA (mRNA), as described more fully, infra. The mRNA codons have the same sequences as the DNA codons of Table 1, except that uracil is found in place of thymine. Complementary trinucleotide DNA sequences having opposite strand polarity are functionally equivalent to the condons of Table 1, as is understood in the art. An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they can result in the production of the same amino acid sequence in all organisms, although certain strains may translate some sequences more efficiently than they do others. Occasionally, a methylated variant of a purine or pyrimidine may be found in a given nucleotide sequence. Such methylations do not affect the coding relationship in any way.

In its basic outline, a method of endowing a microorganism with the ability to synthesize a new protein involves three general steps: (1) isolation and purification of the specific gene or nucleotide sequence containing the genetically coded information for the amino acid sequence of the desired protein, (2) recombination of the isolated nucleotide sequence with an appropriate transfer vector, typically the DNA of a bacteriophage or plasmid, and (3) transfer of the vector to the appropriate microorganism and selection of a strain of the recipient microorganism containing the desired genetic information.

A fundamental difficulty encountered in attempts to exploit commercially the above-described general process lies in the first step, the isolation and purification of the desired specific genetic information. DNA exists in all living cells in the form of extremely high molecular weight chains of nucleotides. A cell may contain more than 10,000 structural genes, coding for the amino acid sequences of over 10,000 specific proteins, each gene having a sequence many hundreds of nucleotides in length. For the most part, four different nucleotide bases make up all the existing sequences. These are adenine (A), guanine (G), cytosine (C), and thymine (T). The long sequences comprising the structural genes of specific proteins are consequently very similar in overall chemical composition and physical properties. The separation of one such sequence from the plethora of other sequences present in isolated DNA cannot ordinarily be accomplished by conventional physical and chemical preparative methods.

Two general methods have been used in the prior art to accomplish step (1) in the above-described general procedure. The first method is sometimes referred to as the shotgun technique. The DNA of an organism is fragmented into segments generally longer than the desired nucleotide sequence. Step (1) of the above-described process is essentially by-passed. The DNA fragments are immediately recombined with the desired vector, without prior purification of specific sequences. Optionally, a crude fractionation step may be interposed. The selection techniques of microbial genetics are relied upon to select, from among all the possibilities, a strain of microorganism containing the desired genetic information. The shotgun procedure suffers from two major disadvantages. Most importantly, the procedure can result in the transfer of hundreds of unknown genes into recipient microorganisms, so that during the experiment, new strains are created, having unknown genetic capabilities. Therefore, the use of such a procedure could create a hazard for laboratory workers and for the environment. A second disadvantage of the shotgun method is that it is extremely inefficient for the production of the desired strain, and is dependent upon the use of a selection technique having sufficient resolution to compensate for the lack of fractionation in the first step.

The second general method takes advantage of the fact that the total genetic information in a cell is seldom, if ever, expressed at any given time. In particular, the differentiated tissues of higher organisms may be synthesizing only a major proportion of the proteins which the organism is capable of making. In extreme cases, such cells may be synthesizing predominantly one protein. In such extreme cases, it has been possible to isolate the nucleotide sequence coding for the protein in question by isolating the corresponding messenger RNA from the appropriate cells.

Messenger RNA functions in the process of converting the nucleotide sequence information of DNA into the amino acid sequence structure of a protein. In the first step of this process, termed transcription, a local segment of DNA having a nucleotide sequence which specifies a protein to be made, is first copied into RNA. RNA is a polynucleotide similar to DNA except that ribose is substituted for deoxyribose and uracil is used in place of thymine. The nucleotide bases in RNA are capable of entering into the same kind of base pairing relationships that are known to exist between the complementary strands of DNA. A and U (T) are complementary, and G and C are complementary. The RNA transcript of a DNA nucleotide sequence will be complementary to the copied sequence. Such RNA is termed messenger RNA (mRNA) because of its status as intermediary between the genetic apparatus of the cell and its protein synthesizing apparatus. Generally, the only mRNA sequences present in the cell at any given time are those which correspond to proteins being actively synthesized at that time. Therefore, a differentiated cell whose function is devoted primarily to the synthesis of a single protein will contain primarily the RNA species corresponding to that protein. In those instances where it is feasible, the isolation and purification of the appropriate nucleotide sequence coding for a given protein can be accomplished by taking advantage of the specialized synthesis of such protein in differentiated cells.

A major disadvantage of the foregoing procedure is that it is applicable only in the relatively rare instances where cells can be found engaged in synthesizing primarily a single protein. The majority of proteins of commercial interest are not synthesized in such a specialized way. The desired proteins may be one of a hundred or so different proteins being produced by the cells of a tissue or organism at a given time. Nevertheless, the mRNA isolation technique is potentially useful since the set of RNA species present in the cell usually represents only a fraction of the total sequences existing in the DNA, and thus provides an initial purification. In order to take advantage of such purification, however, a method is needed whereby sequences present in low frequencies, such as a few percent, can be isolated in high purity.

The present invention provides a process whereby nucleotide sequences can be isolated and purified even when present at a frequency as low as 2% of a heterogeneous population of mRNA sequences. Furthermore, the method may be combined with known methods of fractionating mRNA to isolate and purify sequences present in even lower frequency in the total RNA population as initially isolated. The method is generally applicable to mRNA species extracted from virtually any organism and is therefore expected to provide a powerful basic tool for the ultimate production of proteins of commercial and research interest, in useful quantities.

Human growth hormone has medical utility in the treatment of defective pituitary function. Animal growth hormones have commercial utility in veterinary medicine and in agriculture, particularly in the case of animals used as food sources, where large size and rapid maturation are desirable attributes. Human chorionic somatomammotropin is of medical significance because of its role in the fetal maturation process.

The process of the present invention takes advantage of certain structural features of mRNA and DNA, and makes use of certain enzyme catalyzed reactions. The nature of these reactions and structural details as they are understood in the prior art are described herewith. The symbols and abbreviations used herein are set forth in the following table:

TABLE 2

| | |
|---|---|
| DNA — deoxyribonucleic acid | A — Adenine |
| RNA — ribonucleic acid | T — Thymine |
| cDNA — complementary DNA (enzymatically synthesized from an mRNA sequence) | G — Guanine |
| | C — Cytosine |
| | U — Uracil |
| mRNA — messenger RNA | Tris — 2-Amino-2- |
| dATP — deoxyadenosine triphosphate | hydroxyethyl- |

TABLE 2-continued

| | |
|---|---|
| dGTP — deoxyguanosine triphosphate | 1-1,3-propanediol |
| dGTP — deoxycytidine triphosphate | EDTA — ethylenediamine tetra-acetic acid |
| HCS — Human Chorionic Somatomammotropin | ATP — adenosine triphosphate |
| TCA 13 Trichloroacetic acid | dTTP — thymidine triphosphate |
| HGH — Human Growth Hormone | RGH — Rat growth hormone |

In its native configuration, DNA exists in the form of paired linear polynucleotide strands. The complementary base pairing relationships described above exist between the paired strands such that each nucleotide base of one strand exists opposite its complement on the other strand. The entire sequence of one strand is mirrored by a complementary sequence on the other strand. If the strands are separate, it is possible to synthesize a new partner strand, starting from the appropriate precursor monomers. The sequence of addition of the monomers starting from one end is determined by, and complementary to, the sequence of the original intact polynucleotide strand, which thus serves as a template for the synthesis of its complementary partner. The synthesis of mRNA corresponding to a specific nucleotide sequence of DNA is understood to follow the same basic principle. Therefore a specific mRNA molecule will have a sequence complementary to one strand of DNA and identical to the sequence of the opposite DNA strand, in the region transcribed. Enzymic mechanisms exist within living cells which permit the selective transcription of a particular DNA segment containing the nucleotide sequence for a particular protein. Consequently, isolating the mRNA which contains the nucleotide sequence coding for the amino acid sequence of a particular protein is equivalent to the isolation of the same sequence, or gene, from the DNA itself. If the mRNA is retranscribed to form DNA complementary thereto (cDNA), the exact DNA sequence is thereby reconstituted and can, by appropriate techniques, be inserted into the genetic material of another organism. The two complementary versions of a given sequence are therefore inter-convertible, and functionally equivalent to each other.

The nucleotide subunits of DNA and RNA are linked together by phosphodiester bonds between the 5′ position of one nucleotide sugar and the 3′ position of its next neighbor. Reiteration of such linkages produces a linear polynucleotide which has polarity in the sense that one end can be distinguished from the other. The 3′ end may have a free 3′-hydroxyl, or the hydroxyl may be substituted with a phosphate or a more complex structure. The same is true of the 5′ end. In eucaryotic organisms, i.e., those having a defined nucleus and mitotic apparatus, the synthesis of functional mRNA usually includes the addition of polyadenylic acid to the 3′ end of the mRNA. Messenger RNA can therefore be separated from other classes of RNA isolated from an eucaryotic organism by column chromatography on cellulose to which is attached polythymidylic acid. See Aviv, H., and Leder, P., *Proc.Nat. Acad.Sci. USA* 69, 1408 (1972). Other chromatographic methods, exploiting the base-pairing affinity of poly A for chromatographic packing materials containing oligo dT, poly U, or combinations of poly T and poly U, for example, poly U-Sepharose, are likewise suitable.

Reverse transcriptase catalyzes the synthesis of DNA complementary to an RNA template strand in the presence of the RNA template, a primer which may be any complementary oligo or polynucleotide having a 3′-hydroxyl, and the four deoxynucleoside triphosphates, dATP, dGTP, dCTP, and dTTP. The reaction is initiated by the non-covalent association of the oligodeoxynucleotide primer near the 3′ end of mRNA followed by stepwise addition of the appropriate deoxynucleotides, as determined by base-pairing relationships with the mRNA nucleotide sequence, to the 3′ end of the growing chain. The product molecule may be described as a hairpin structure in which the original RNA is paired by hydrogen bonding with a complementary strand of DNA partly folded back upon itself at one end. The DNA and RNA strands are not covalently joined to each other. Reverse transcriptase is also capable of catalyzing a similar reaction using a single-stranded DNA template, in which case the resulting product is a double-stranded DNA hairpin having a loop of single-stranded DNA joining one set of ends. See Aviv, H. and Leder, P., *Proc.Natl.Acad.Sci.* USA 69, 1408 (1972) and Efstratiadis, A., Kafatos, F. C., Maxam, A. M., and Maniatis, T., *Cell* 7, 279 (1976).

Restriction endonucleases are enzymes capable of hydrolyzing phosphodiester bonds in DNA, thereby creating a break in the continuity of the DNA strand. If the DNA is in the form of a closed loop, the loop is converted to a linear structure. The principal feature of a restriction enzyme is that its hydrolytic action is exerted only at a point where a specific nucleotide sequence occurs. Such a sequence is termed the restriction site for the restriction endonuclease. Restriction endonucleases from a variety of sources have been isolated and characterized in terms of the nucleotide sequence of their restriction sites. When acting on double-stranded DNA, some restriction endonucleases hydrolyze the phosphodiester bonds on both strands at the same point, producing blunt ends. Others catalyze hydrolysis of bonds separated by a few nucleotides from each other, producing free single-stranded regions at each end of the cleaved molecule. Such single-stranded ends are self-complementary, hence cohesive, and may be used to rejoin the hydrolyzed DNA. Since any DNA susceptible to cleavage by such an enzyme must contain the same recognition site, the same cohesive ends will be produced, so that it is possible to join heterogeneous sequences of DNA which have been treated with restriction endonuclease to other sequences similarly treated. See Roberts, R. J., *Crit.Rev.Biochem.* 4, 123 (1976).

It has been observed that restriction sites for a given enzyme are relatively rare and are nonuniformly distributed. Whether a specific restriction site exists within a given segment is a matter which must be empirically determined. However, there is a large and growing number of restriction endonucleases, isolated from a variety of sources with varied site specificity, so that there is a reasonable probability that a given segment of a thousand nucleotides will contain one or more restriction sites.

For general background see Watson, J. D., *The Molecular Biology of the Gene,* 3d Ed., Benjamin, Menlo Park, Calif., (1976); Davidson, J. N., *The Biochemistry of the Nucleic Acids,* 8th Ed., Revised by Adams, R. L. P., Burdon, R. H., Campbell, A. M. and Smellie, R. M. S., Academic Press, New York, (1976); and Hayes, W., "The Genetics of Bacteria and Their Viruses", *Studies*

*in Basic Genetics and Molecular Biology,* 2d Ed., Blackwell Scientific Pub., Oxford (1968).

SUMMARY OF INVENTION

A novel purification procedure of cDNA of desired nucleotide sequence complementary to an individual mRNA species is disclosed. The method employs restriction endonuclease cleavage of cDNA transcribed from a complex mixture of mRNA. The method does not require any extensive purification of RNA but instead makes use of transcription of RNA into cDNA, the sequence specific fragmentation of this cDNA with one or two restriction endonucleases, and the fractionation of the cDNA restriction fragments on the basis of their length. The use of restriction endonucleases eliminates size heterogeneity and produces homogeneous length DNA fragments from any cDNA species which contains at least two restriction sites. From the initially heterogeneous population of cDNA transcripts, uniform size fragments of desired sequence are produced. The fragments may be several hundred nucleotides in length and may in some instances include the entire structural gene for the desired protein. The length of the fragments depends on the number of nucleotides separating the restriction sites and will usually be different for different regions of DNA. Fractionation by length enables purification of a homogeneous population of fragments having the desired sequence. The fragments will be homogeneous in size and highly pure in terms of nucleotide sequence. Current separation and analysis methods enable the isolation of such fragments from a corresponding mRNA species representing at least 2% of the mass of the RNA transcribed. The use of prior art RNA fractionation methods to prepurify the mRNA before transcription will result in lowering the actual lower limit of detection to less than 2% of the total mRNA isolated from the organism.

Specific sequences purified by the procedure outlined above may be further purified by a second specific cleavage with a restriction endonuclease capable of cleaving the desired sequence at an internal site. This cleavage results in formation of two sub-fragments of the desired sequence, separable on the basis of their lengths. The sub-fragments are separated from uncleaved and specifically cleaved contaminating sequences having substantially the same original size. The method is founded upon the rarity and randomness of placement of restriction endonuclease recognition sites, which results in an extremely low probability that a contaminant having the same original length will be cleaved by the same enzyme to yield fragments having the same length as those yielded by the desired sequence. After separation from the contaminants, the sub-fragments of the desired sequence may be rejoined using techniques known in the art to reconstitute the original sequence. The two sub-fragments must be prevented from joining together in the reverse order of their original sequence. A method is disclosed whereby the sub-fragments can only join to each other in the proper order.

Variations of the above-recited methods may be used in combination with appropriate labelling techniques to obtain accurate, quantitative measurements of the purity of the isolated sequences. The combined techniques have been applied to produce a known nucleotide sequence with greater than 99% purity.

The cDNA isolated and purified by the described methods may be recombined with a suitable transfer vector and transferred to a suitable host microorganism. Novel plasmids have been produced, containing the nucleotide sequences coding for rat growth hormone and the major portions of human chorionic somatomammotropin and human growth hormone, respectively. Novel microorganisms have been produced having as part of their genetic makeup the genes coding for RGH, the major portion of HCS and the major portion of HGH, respectively. The disclosed techniques may be used for the isolation and purification of growth hormones from other animal species and for the construction of novel transfer vectors and microorganisms containing these genes.

DETAILED DESCRIPTION OF INVENTION

The present invention employs as starting material polyadenylated, crude or partially purified messenger RNA, which may be heterogeneous in sequence and in molecular size. The selectivity of the RNA isolation procedure is enhanced by any method which results in an enrichment of the desired mRNA in the heterodisperse population of mRNA isolated. Any such prepurification method may be employed in conjunction with the method of the present invention, provided the method does not introduce endonucleolytic cleavage of the mRNA. An important initial consideration is the selection of an appropriate source tissue for the desired mRNA. Often, this choice will be dictated by the fact that the protein ultimately to be produced is only made by a certain specialized tissue of a differentiated organism. Such is the case, for example, with the peptide hormones, such as growth hormone or HCS. In other cases, it will be found that a variety of cell types or microbial species can serve as a source of the desired mRNA. In those cases, some preliminary experimentation will be necessary in order to determine the optimal source. Frequently, it will be found that the proportion of desired mRNA can be increased by taking advantage of cellular responses to environmental stimuli. For example, treatment with a hormone may cause increased production of the desired mRNA. Other techniques include growth at a particular temperature and exposure to a specific nutrient or other chemical substance.

Prepurification to enrich for desired mRNA sequences may also be carried out using conventional methods for fractionating RNA, after its isolation from the cell. Any technique which does not result in degradation of the RNA may be employed. The techniques of preparative sedimentation in a sucrose gradient and gel electrophoresis are especially suitable.

The mRNA must be isolated from the source cells under conditions which preclude degradation of the mRNA. The action of RNase enzymes is particularly to be avoided because these enzymes are capable of hydrolytic cleavage of the RNA nucleotide sequence. The hydrolysis of one bond in the sequence results in disruption of that sequence and loss of the RNA fragment containing the original 5′ end of the sequence. A suitable method for inhibiting RNase during extraction from cells is disclosed in U.S. application Ser. No. 805,023, now abandoned incorporated herein by reference, assigned to the same assignee as the instant application. The method involves the use of 4 M guanidinium thiocyanate and 1 M mercaptoethanol during the cell disruption step. In addition, a low temperature and a pH near 5.0 are helpful in further reducing RNase degradation of the isolated RNA.

Prior to application of the method of the present invention, mRNA must be prepared essentially free of contaminating protein, DNA, polysaccharides and lipids. Standard methods are well known in the art for accomplishing such purification. RNA thus isolated contains non-messenger as well as messenger RNA. A convenient method for separating the mRNA of eucaryotes is chromatography on columns of oligo-dT cellulose, or other oligonucleotide-substituted column material such a poly U-Sepharose, taking advantage of the hydrogen bonding specificity conferred by the presence of polyadenylic acid on the 3′ end of eucaryotic mRNA.

The initial step in the process of the present invention is the formation of DNA complementary to the isolated heterogeneous sequences of mRNA. The enzyme of choice for this reaction is reverse transcriptase, although in principle any enzyme capable of forming a faithful complementary DNA copy of the mRNA template could be used. The reaction may be carried out under conditions described in the prior art, using mRNA as a template and a mixture of the four deoxynucleoside triphosphates dATP, dGTP, dCTP and dTTP, as precursors for the DNA strand. It is convenient to provide that one of the deoxynucleoside triphosphates be labeled with a radioisotope, for example $^{32}P$ in the alpha position, in order to monitor the course of the reaction, to provide a tag for recovering the product after separation procedures such as chromatography and electrophoresis, and for the purpose of making quantitative estimates of recovery. See Efstratiadis, A., et al., supra.

The cDNA transcripts produced by the reverse transcriptase reaction are somewhat heterogeneous with respect to sequences at the 5′ end and the 3′ end due to variations in the initiation and termination points of individual transcripts, relative to the mRNA template. The variability at the 5′ end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and a variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

The indeterminacy at the 3′-end of the cDNA transcript is due to a variety of factors affecting the reverse transcriptase reaction, and to the possibility of partial degradation of the RNA template. The isolation of specific cDNA transcripts of maximal length is greatly facilitated if conditions for the reverse transcriptase reaction are chosen which not only favor full length synthesis but also repress the synthesis of small DNA chains. Preferred reaction conditions for avian myeloblastosis virus reverse transcriptase are given in the examples section. The specific parameters which may be varied to provide maximal production of long-chain DNA transcripts of high fidelity are reaction temperature, salt concentration, amount of enzyme, concentration of primer relative to template, and reaction time.

The conditions of temperature and salt concentration are chosen so as to optimize specific base-pairing between the oligo-dT primer and the polyadenylated portion of the RNA template. Under properly chosen conditions, the primer will be able to bind at the polyadenylated region of the RNA template, but non-specific initiation due to primer binding at other locations on the template, such as short, A-rich sequences, will be substantially prevented. The effects of temperature and salt are interdependent. Higher temperatures and lower salt concentrations decrease the stability of specific base-pairing interactions. The reaction time is kept as short as possible, in order to prevent non-specific initiations and to minimize the opportunity for degradation. Reaction times are interrelated with temperature, lower temperatures requiring longer reaction times. At 42° C., reactions ranging from 1 min. to 10 minutes are suitable. The primer should be present in 50 to 500-fold molar excess over the RNA template and the enzyme should be present in similar molar excess over the RNA template. The use of excess enzyme and primer enhances initiation and cDNA chain growth so that long-chain cDNA transcripts are produced efficiently within the confines of the sort incubation times.

In many cases, it will be possible to carry out the remainder of the purification process of the present invention using single-stranded cDNA sequences transcribed from mRNA. However, as discussed below, there may be instances in which the desired restriction enzyme is one which acts only on double-stranded DNA. In these cases, the cDNA prepared as described above may be used as a template for the synthesis of double-stranded DNA, using a DNA polymerase such as reverse transcriptase and a nuclease capable of hydrolyzing single-stranded DNA. Methods for preparing double-stranned DNA in this manner have been described in the prior art. See, for example, Ullrich, A., Shine, J., Chirgwin, J., Pictet, R., Tischer, E., Rutter, W. J. and Goodman, H. M., *Science* 196, 1313 (1977).

Heterogeneous cDNA, prepared by transcription of heterogeneous mRNA sequences, is then treated with one or two restriction endonucleases. The choice of endonuclease to be used depends in the first instance upon a prior determination that recognition sites for the enzyme exist in the sequence of the cDNA to be isolated. The method depends upon the existence of two such sites. If the sites are identical, a single enzyme will be sufficient. The desired sequence will be cleaved at both sites, eliminating size heterogeneity as far as the desired cDNA sequence is concerned, and creating a population of molecules, termed fragments, containing the desired sequence and homogeneous in length. If the restriction sites are different, two enzymes will be required in order to produce the desired homogeneous length fragments.

The choice of restriction enzyme(s) capable of producing an optimal length nucleotide sequence fragment coding for all or part of the desired protein must be made empirically. If the amino acid sequence of the desired protein is known, it is possible to compare the nucleotide sequence of uniform length nucleotide fragments produced by restriction endonuclease cleavage with the amino acid sequence for which it codes, using the known relationship of the genetic code common to all forms of life. A complete amino acid sequence for the desired protein is not necessary, however, since a reasonably accurate identification may be made on the basis of a partial sequence. Where the amino acid sequence of the desired protein is now known, the uniform length polynucleotides produced by restriction endonuclease cleavage may be used as probes capable of identifying the synthesis of the desired protein in an appropriate in vitro protein synthesizing system. Alternatively, the mRNA may be purified by affinity chromatography. Other techniques which may be suggested to those skilled in the art will be appropriate for this purpose.

The number of restriction enzymes suitable for use depends upon whether single-stranded or double-stranded cDNA is used. The preferred enzymes are those capable of acting on single-stranded DNA, which is the immediate reaction product of mRNA reverse transcription. The number of restriction enzymes now known to be capable of acting on single-stranded DNA is limited. The enzymes HaeIII, HhaI and Hin(f)I are presently known to be suitable. In addition, the enzyme MboII may act on single-stranded DNA. Where further study reveals that other restriction enzymes can act on single-stranded DNA, such other enzymes may appropriately be included in the list of preferred enzymes. Additional suitable enzymes include those specified for double-stranded cDNA. Such enzymes are not preferred since additional reactions are required in order to produce double-stranded cDNA, providing increased opportunities for the loss of longer sequences and for other losses due to incomplete recovery. The use of double-stranded cDNA presents the additional technical disadvantage that subsequent sequence analysis is more complex and laborious. For these reasons, single-stranded cDNA is preferred, but the use of double-stranded DNA is feasible.

The cDNA prepared for restriction endonuclease treatment may be radioactively labeled so that it may be detected after subsequent separation steps. A preferred technique is to incorporate a radioactive label such as $^{32}P$ in the alpha position of one of the four deoxynucleoside triphosphate precursors. Highest activity is obtained when the concentration of radioactie precursor is high relative to the concentration of the non-radioactive form. However, the total concentration of any deoxynucleoside triphosphate should be greater than 30 $\mu M$, in order to maximize the length of cDNA obtained in the reverse transcriptase reaction. See Efstratiadis, A., Maniatis, T., Kafatos, F. C., Jeffrey, A., and Vournakis, J. N., Cell 4, 367 (1975). For the purpose of determining the nucleotide sequence of cDNA, the 5′ ends may be conveniently labeled with $^{32}P$ in a reaction catalyzed by the enzyme polynucleotide kinase. See Maxam, A. M. and Gilbert, W., *Proc.Natl.Acad.Sci. USA* 74, 560 (1977).

Fragments which have been produced by the action of a restriction enzyme or combination of two restriction enzymes may be separated from each other and from heterodisperse sequences lacking recognition sites by any appropriate technique capable of separating polynucleotides on the basis of differences in length. Such methods include a variety of electrophoretic techniques and sedimentation techniques using an ultracentrifuge. Gel electrophoresis is preferred because it provides the best resolution on the basis of polynucleotide length. In addition, the method readily permits quantitative recovery of separated materials. Convenient gel electrophoresis methods have been described by Dingman, C. W., and Peacock, A. C., *Biochemistry* 7, 659 (1968), and by Maniatis, T., Jeffrey, A. and van de Sande, H., *Biochemistry* 14, 3787 (1975).

Prior to restriction endonuclease treatment, cDNA transcripts obtained from most sources will be found to be heterodisperse in length. By the action of a properly chosen restriction endonuclease, or pair of endonucleases, polynucleotide chains containing the desired sequence will be cleaved at the respective restriction sites to yield polynucleotide fragments of uniform length. Upon gel electrophoresis, these will be observed to form a distinct band. Depending on the presence or absence of restriction sites on other sequences, other discrete bands may be formed as well, which will most likely be of different length than that of the desired sequence. Therefore, as a consequence of restriction endonuclease action, the gel electrophoresis pattern will reveal the appearance of one or more discrete bands, while the remainder of the cDNA will continue to be heterodisperse. In the case where the desired cDNA sequence comprises the major polynucleotide species present, the electrophoresis pattern will reveal that most of the cDNA is present in the discrete band.

Although it is unlikely that two different sequences will be cleaved by restriction enzymes to yield fragments of essentially similar length, a method for determining the purity of the defined length fragments is desirable. Sequence analysis of the electrophoresis band may be used to detect impurities representing 10% or more of the material in the band. A method for detecting lower levels of impurities has been developed, as part of the present invention, founded upon the same general principles applied in the initial isolation method. The method requires that the desired nucleotide sequence fragment contain a recognition site for a restriction endonuclease not employed in the initial isolation. Treatment of polynucleotide material, eluted from a gel electrophoresis band, with a restriction endonulcease capable of acting internally upon the desired sequence will result in cleavage of the desired sequence into two sub-fragments, most probably of unequal length. These sub-fragments upon electrophoresis will form two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method. A quantitative measure of the purity of the fragments of desired sequence can be obtained by comparing the relative amounts of material present in those bands representing sub-fragments of the desired sequence with the total amount of material.

Following the foregoing separation, the desired sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. See Sgaramella, V., Van de Sande, J. H., and Khorana, H. G., *Proc.Natl.Acad.Sci. USA* 67, 1468 (1970). Where the sequences to be joined are not blunt-ended, the ligase obtained from E. Coli may be used, Modrich, P., and Lehman, I. R., *J. Biol. Chem.* 245, 3626 (1970).

The efficiency of reconstituting the original sequence from sub-fragments produced by restriction endonuclease treatment will be greatly enhanced by the use of a method for preventing reconstitution in improper sequence. This unwanted result is prevented by treatment of the homogenous length cDNA fragment of desired sequence with an agent capable of removing the 5'-terminal phosphate groups on the cDNA prior to cleavage of the homogenous cDNA with a restriction endonuclease. The enzyme, alkaline phosphatase, is preferred. The 5'-terminal phosphate groups are a structural prerequisite for the subsequent joining action of DNA ligase used to reconstitute the cleaved sub-fragments. Therefore, ends which lack a 5'-terminal phosphate cannot be covalently joined. The DNA sub-fragments can only be joined at the ends containing a 5'-phosphate generated by the restriction endonuclease cleavage performed on the isolated DNA fragments. The method is essentially that described in detail in U.S. application Ser. No. 805,023.

The majority of cDNA transcripts, under the conditions employed, are derived from the mRNA region contaning the 5'-end of the mRNA template by specifically priming on the same template with a fragment obtained by restriction endonuclease cleavage. In this way, the above-described method may be used to obtain not only fragments of specific nucleotide sequence related to a desired protein, but also the entire nucleotide sequence coding for the protein of interest. The purification process is of a special significance in the cloning of human genes, which, under Federal regulations, can only be put into recombinant DNA and then into bacteria after the genes have been very carefully purified, or if the experiments are carried out in special high-risk (P4) facilities. See Federal Register, Vol. 41, No. 131, July 7, 1967, pp 27902–27943. The present method has enabled the production of sufficiently pure human genes, comprising the majority of the structure of HCS and HGH. Human genetic material, isolated and purified as described above, may be incorporated into recombinant plasmids or other transfer vectors. Doublestranded chemically synthesized oligonucleotide linkers, containing the recognition sequence for a restriction endonuclease, may be attached to the ends of the isolated cDNA, to facilitate subsequent enzymatic removal of the human gene portion from the transfer vector DNA. See Scheller, R. H., et al., *Science* 196, 177 (1977). The transfer vector DNA is converted from a continuous loop to a linear form by treatment with an appropriate restriction endonuclease. The ends thereby formed are treated with alkaline phosphatase to remove 5'-phosphate and groups so that the transfer vector DNA may not reform a continuous loop in a DNA ligase reaction without first incorporating a segment of the human DNA. The cDNA, with attached linker oligonucleotides, and the treated transfer vector DNA are mixed together with a DNA ligase enzyme, to join the cDNA to the vector DNA, forming a continuous loop of recombinant vector DNA having the cDNA incorporated therein. Where a plasmid transfer vector is used, usually the closed loop will be the only form able to transform a bacterium. Transformation, as is understood in the art and used herein, is the term used to denote the process whereby a microorganism incorporates extracellular DNA into its own genetic constitution. Plasmid DNA in the form of a closed loop may be so incorporated under appropriate environmental conditions. The incorporated closed loop plasmid undergoes replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used. Once a recombinant transfer vector has been made, transformation of a suitable microorganism is a straightforward process, and novel microorganisms strains containing the human gene may readily be isolated, using appropriate selection techniques, as understood in the art.

The construction of novel transfer vectors and microorganisms containing the rat growth hormone gene can be carried out in similar fashion, except that a simplified process is permitted by lower purity requirements. Following isolation of the initial cDNA transcripts of rat pituitary mRNA and electrophoresis to fractionate the cDNA transcripts by length, a band of material migrating at the expected position for full-length RGH-cDNA may be used as the starting material for the cloning process. This method is advantageous over the method employed for the human genes in that it permits the isolation of DNA containing the entire structural gene nucleotide sequence. The growth hormones of vertebrate species are similar in length and in amino acid sequence. Therefore the foregoing procedure could be applied to the cloning of any growth hormone from an animal source and would be applicable to the isolation of the full sequence of human growth hormone given suitable (P4) laboratory facilities or a relaxation of the current Federal purity requirements. Although it is preferred to isolate cDNA appearing as an observable band after gel electrophoresis, it would be feasible to isolate cDNA at the expected position in the absence of a discrete band, provided the approximate length of the desired sequence were known.

Using the above-described methods for purification and analysis, a desired nucleotide sequence containing most of the structural gene for HCS has been isolated and shown to be greater than 99% pure. The structural gene for HGH has been isolated to a comparable degree of purity. Novel plasmids containing the isolated HCS or HGH sequences have been synthesized. Novel microorganisms containing the isolated HCS or HGH sequences as part of their genetic material have been produced. A nucleotide sequence containing the entire structural gene for RGH has been isolated, novel recombinant plasmids constructed therewith. Novel microorganisms containing the structural gene for RGH as part of their genetic makeup have been produced.

BRIEF DESCRIPTION OF THE FIGURES

The accompanying figures and drawing are provided to demonstrate the results obtained in the specific examples illustrating the invention.

EXAMPLE 1

Figure 3:
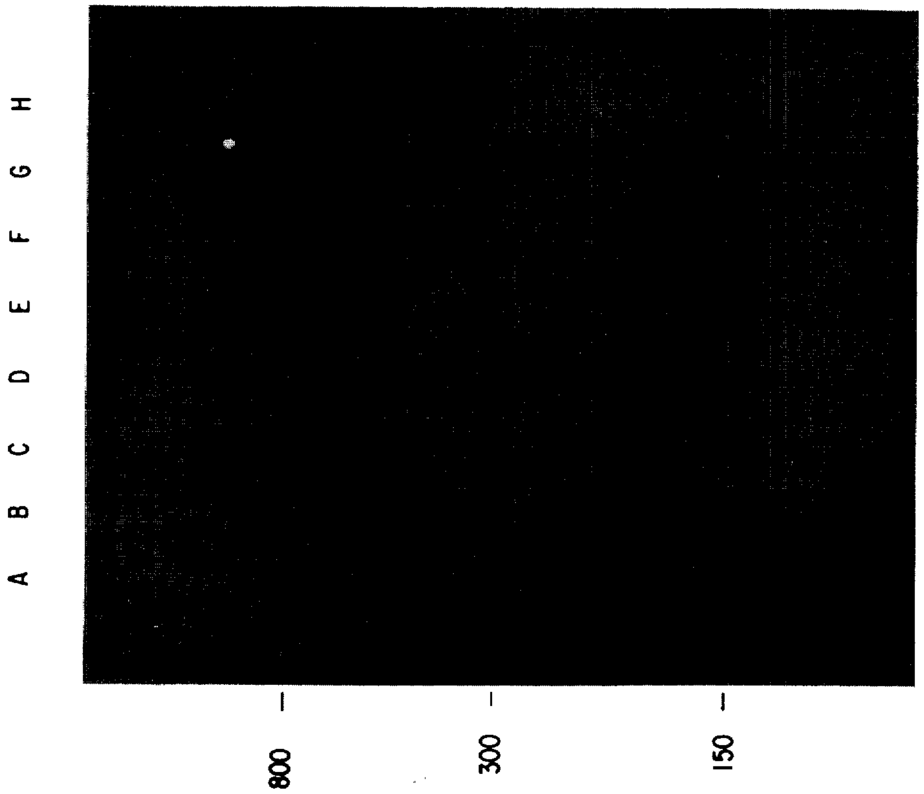
FIG. 3 is an autoradiogram of gel electrophoresis results using $^{32}P$-labeled cDNA, as described in detail in example 2.

The general procedure for isolating a specific cDNA sequence has been demonstrated by isolating a sequence comprising a portion of the coding region for HCS, extracted from placental tissue.

mRNA EXTRACTION FROM PLACENTA

Human term placentas obtained from cesarean section were quickfrozen in liquid nitrogen and stored at −60° C. For extraction of total RNA, 40 g of the frozen placental tissue was broken into small pieces and dissolved with the aid of a blender in 140 ml of freshly prepared 7 M guanidinium-HCl (Cox, R. A., *Methods in Enzymology* 12, 120 (1968), 20 mM Tris-Hcl, pH 7.5, 1 mM EDTA, 1% sarcosyl* at 0° C. After adding 0.5 g CsCl to each ml, the dark brown solution was heated at 65° C. for 5 min., quick-cooled in ice, layered on top of a 5 ml cushion of 5.7 M CsCl, 10 mM Tris-HCl, pH 7.5, 1 mM EDTA in 1 in.×3½ in. nitrocellulose tube and centrifuged in an SW27 rotor (Beckman Instruments Corp., Fullerton, Calif.) at 27,000 rpm for 16 hr at 15° C. (Glisin, V., Crkvenjakov, R., and Ryus, C., *Biochem.* 13, 2633 (1974)). After centrifugation, the tube contents were decanted, the tubes were drained, and the bottom ½ cm containing the clear RNA pellet was cut off with a razor blade. Pellets were transferred into a sterile erlenmeyer flask and dissolved in 20 ml 10 mM Tris-HCl, pH 7.5, 1 mM EDTA, 5% sarcosyl and 5% phenol. The solution was then made 0.1 M in NaCl and vigorously shaken with 40 ml of a 50% phenol-50% chloroform mixture. RNA was precipitated from the aqueous phase with ethanol in the presence of 0.2 M Na-acetate pH 5.5. RNA pellets were washed with 95% ethanol, dried, and dissolved in sterile water. Usually 40 g of placental tissue yielded about 30 mg of RNA from which approximately 300 ug of polyadenylated RNA was obtained after twice chromatographing on oligo-dT cellulose. See Aviv, and Leder, supra.

*Trademark, Ciba-Geigy Corp., Greensboro, N.C.

SYNTHESIS OF cDNA

Analytical reactions were performed in 5 μl containing 50 mM Tris-HCl, pH 8.3; 0.1 mM EDTA; 7 mM $MgCl_2$; 20 mM KCl; 10 mM β-mercaptoethanol; 40 μM dCTP (50,000 cpm $^{32}P$ per pmole); 500 μM each dCTP, dATP, and dTTP; 100 μg/ml of polyadenylated RNA; 20 μg/ml oligo-$dT_{12\text{-}18}$ obtained from Collaborative Research, Waltham, Mass.; and 100 units/ml reverse transcriptase from avian myeloblastosis virus. The enzyme is available from Dr. D. J. Beard, Life Science Incorporated, St. Petersburg, Fla., who produces the enzyme under contract with the National Institutes of Health, by the procedure of Kacian, D. L. and Spiegelman, S., in *Methods of Enzymology* 29, L. Grossman, and K. Moldave, eds., Academic Press, N.Y. (1974), p. 150. Reactions were started by the addition of enzyme at 0° C. and synthesis was for 6 min at 42° C. Under these conditions approximately $10^6$ cpm $^{32}P$ were incorporated into TCA-precipitable material and each ug of RNA yielded about 50 ng of cDNA. To obtain enough cDNA for sequence analysis, the reaction volumes were increased to 100 μl and the dCTP concentration was raised to 250 μM (specific activity of 500 cpm $^{32}P$ per pmole). Under these conditions about 200,000 cpm of $^{32}P$-labeled dCMP were incorporated into cDNA.

RESTRICTION ENDONUCLEASE TREATMENT

For restriction endonuclease digestions the analytical reactions were stopped by the addition of 20 μl of ice-cold water, boiled for 2 min, quick-cooled on ice, and made 7 mM in $MgCl_2$. Aliquots (5 μl, about $2\times10^5$ cpm) were digested using an excess amount of restriction endonuclease(s) HaeIII or HhaI or both, for 1 hr at 37° C. HaeIII was prepared according to the method of Middleton, J. H., Edgell, M. H., and Hutchinson, C. A. III, *J. Virol.* 10, 42 (1972). HhaI and HpaII were obtained from New England Bio-Labs, Beverly, Mass. HaeII is also available from the latter source. The amount of enzyme used was empirically determined to be in excess of the amount needed to completely digest an equivalent amount of restriction-sensitive DNA under identical reaction conditions. Reactions were stopped with 5 μl of 20 mM EDTA, 20% sucrose, 0.05% bromophenolblue, heated to 100° C. for 1 min and then analyzed by polyacrylamide gel electrophoresis. The products were separated on a composite 4.5%–10% polyacrylamide slab gel for 2.5 hr at 150 V in Tris-Borate-EDTA buffer (Dingman, C. W. and Peacock, A. C., supra) and visualized by autoradiography of the dry gel.

Figure 1:
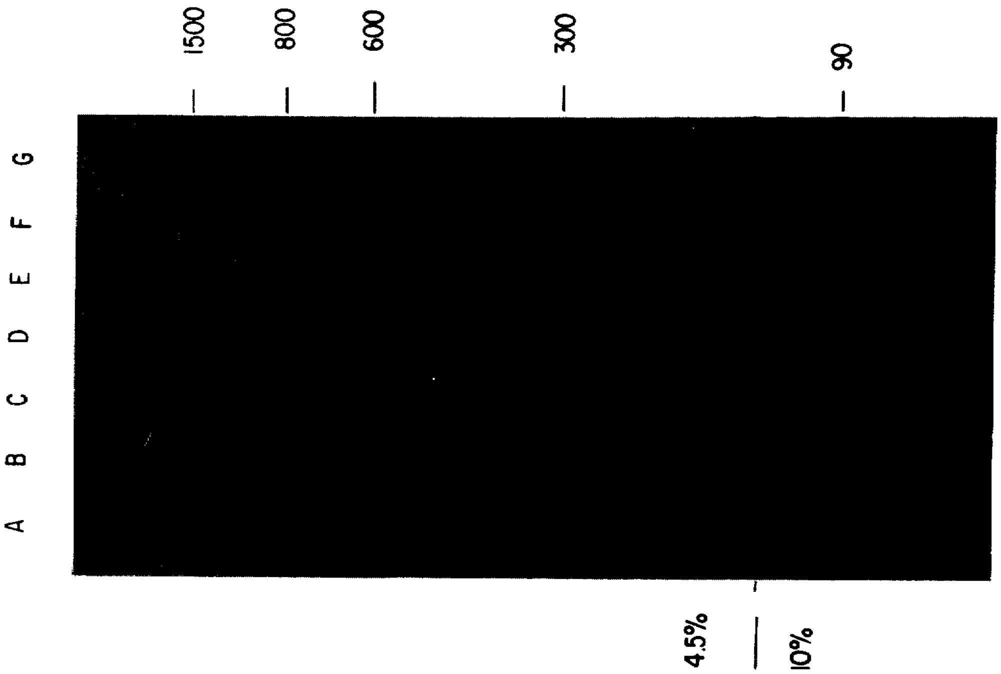
FIG. 1 is an autoradiogram of a series of gel electrophoresis runs of $^{32}P$-labeled cDNA, as described in detail in example 1.

FIG. 1 shows the results of gel electrophoresis and autoradiography of $^{32}P$-labeled cDNA, prepared as described above. The samples were initially spotted at the origin and migrated electrophoretically through 4.5% acrylamide and then through 10% acrylamide. A bar is placed on the left-hand side of the figure to indicate the position of the boundary between the two gel regions. Lane A represents the electrophoretic migration of the total cDNA transcript. Lane B shows the migration of HhaI treated cDNA. Lane C shows the migration of HaeIII treated cDNA. Lane D shows the electrophoretic migration of total cDNA treated with both HhaI and HaeIII. Lane E demonstrates the electrophoretic migration of the material isolated from the prominent band in Lane C. Land F shows electrophoretic migration of isolated material from the prominent band of Lane C after treatment with HhaI. Lane G shows the electrophoretic migration of HaeIII cleaved 5′-$^{32}P$ end-labeled single-stranded phage M13 DNA used as a size standard, according to Horiuchi, K., and Zinder, N. D., *Proc. Nat. Acad. Sci.* USA 72, 2555 (1975). The approximate lengths in nucleotides of these DNA fragments are indicated by the numbers on the right.

The result in Lane A demonstrates that the cDNA transcript from term placental mRNA is heterodisperse. Treatment with HhaI, Lane B or HaeIII, Lane C results in the accumulation of polynucleotides of discrete length. The production of such discrete bands indicates the presence, in a heterogeneous population of cDNA transcripts, of at least one sequence present in multiple copies and having two restriction sites for HhaI and HaeIII, respectively. Cleavage with HhaI produces a fragment of about 470 nucleotides, and HaeIII digestion produces a fragment of approximately 550 nucleotides in length. Digestion by both enzymes yields three fragments designated A, 90 nucleotides long, B, 460 nucleotides long, and C, approximately 10 nucleotides long. Due to its small size, fragment C migrated off the gel under the conditions used in FIG. 1. The band of material appearing at the interface between 10% and 4.5% gel represents heterogeneous material which was too large to enter the 10% gel and therefore accumulated at the interface. As judged from the simple band pattern of Lane D, fragments A and B seem to originate from the same cDNA molecule. This conclusion was confirmed by elution of the larger HaeIII fragment from the gel, migrating as shown in Lane E, followed by redigestion with HhaI. such treatment produced two fragments comigrating with the bands released by combined HaeIII and HhaI digestion of the total cDNA, as seen by comparing Lanes D and F. In the total cDNA digest, Lane D, the autoradiographic density, which is a measure of the total radioactivity present in the band, is greater for fragment A than fragment B, although the reverse may be expected on the basis of size differences. This observation suggests that fragment A is transcribed from a region closer to the 3'-end of the mRNA than is fragment B.

Figure 2:
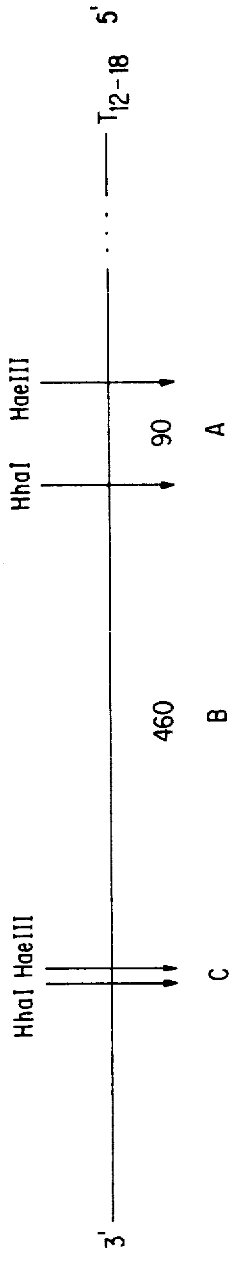
FIG. 2 is a schematic representation of the nucleotide sequence coding for HCS, showing the relative locations of various restriction sites, as described in detail in example 1.

FIG. 2 is a schematic representation of the cDNA molecule showing the relative locations of the HaeIII and HhaI restriction sites. DNA fragments A and B, derived from the same cDNA molecule, were ordered on the basis of their relative intensity on the autoradiogram shown in FIG. 1, Lane D. The existence of DNA fragment C was inferred from the difference in the electrophoretic mobility of the band appearing in Lane B and Lane D of FIG. 1. The size of DNA fragment A is known exactly from a determination of its nucleotide sequence by the method of Maxam, A. and Gilbert, W., supra. The size of DNA fragment B was determined by comparison with the M13 DNA size markers shown in FIG. 1, Lane G.

The nucleotide sequences of DNA fragment A and a portion of the 5'-end of fragment B were determined by the procedure of Maxam, A. and Gilbert, W., supra. Since the amino acid sequence of HCS is known, the nucleotide sequence of the two fragments could be compared with the amino acid sequence, using the known relationships of the genetic code. On the basis of these relationships it was demonstrated that the specific sequences did in fact code for portions of the HCS molcule, and further confirmed the ordering of these fragments shown in FIG. 2.

EXAMPLE 2

The ability of the process of the present invention to purify a desired nucleotide sequence that is a minority proportion of the total population of nucleotide sequences is demonstrated in the following reconstruction experiment. Defined RNA mixtures containing purified rabbit globin RNA and human polyadenylated placental RNA were used as template for reverse transcriptase in the presence of alpha-$^{32}$P dCTP, final specific activity, $10^5$ cpm per pmole. The cDNA products were cleaved with endonuclease HaeIII and the cleavage products were separated on 4.5%-10% composite polyacrylamide slab gel. The cDNA fragments were visualized by autoradiography of the dried gel.

FIG. 3 shows the results of the experiments. The gels were run essentially as described in example 1. Size markers prepared by endonuclease HaeIII cleavage of phage M13 DNA and 5'-$^{32}$P end labelling of the fragments thereby produced, were run in lanes A and H. The approximate lengths in nucleotides of these DNA fragments are indicated by the numbers on the left. Lanes B-G show the electrophoresis patterns produced by initiating the foregoing sequence of reactions with mixtures of globin RNA and placental RNA in varying proportions, as shown in the following table.

TABLE 3

| Lane | Globin RNA nanograms | Placental RNA nanograms |
|---|---|---|
| B | 300 | 0 |
| C | 60 | 240 |
| D | 30 | 270 |
| E | 15 | 285 |
| F | 7.5 | 292.5 |
| G | 0 | 300 |

It can be seen that a 320 nucleotide using HaeIII fragment is derived from globin cDNA. The globin cDNA transcript can still be detected if globin RNA represents as little as 2-5% of the total RNA. If an RNA species is present as isolated in too low a copy number to be amenable to this mode of analysis, it can be first partially purified by any one of the known RNA purification schemes until it represents about 2-5% of the remaining species mixture.

EXAMPLE 3

The purification of a nucleotide sequence fragment approximately 550 base-pairs in length comprising a portion of the coding region for HCS is described, together with a method of measuring the purity of the isolated sequence. The purified fragment is demonstrated to be greater than 99% pure.

PURIFICATION OF HCS cDNA

Figure 4:
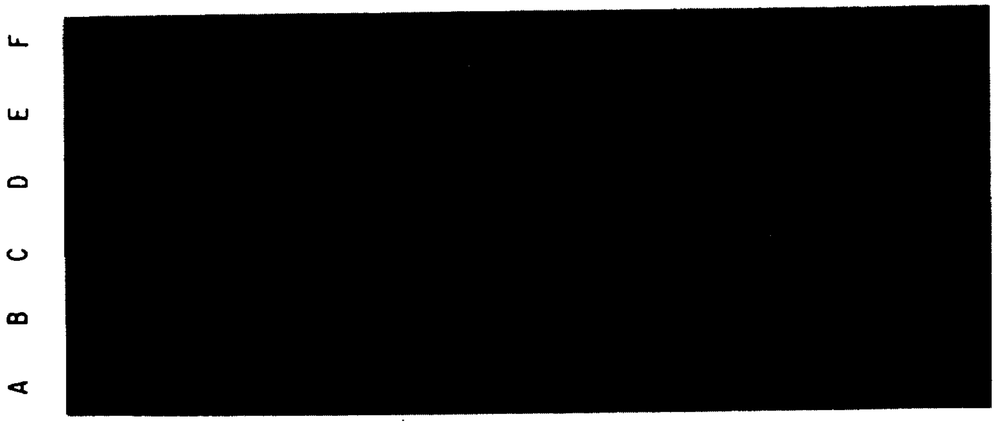

Polyadenylated placental RNA isolated as described in example 1 was enriched for HCS mRNA by sedimentation in a 5% to 20% (w/v) sucrose gradient at 4° C. in the SW 27 rotor of a Beckman Instruments ultracentrifuge at 25,000 rpm for 16 hours. The 11S-14S region of the gradient was pooled and 100 μg of this RNA used for the synthesis of double-stranded cDNA as described by Ullrich, A., et al., supra. Synthesis of the second strand was stopped by extraction of the reaction mixture with one volume of ethanol at −70° C. Digestion of the cDNA with HaeIII endonuclease was carried out in 50 μl of 6 mM Tris-Hcl, pH 7.5, 6 mM $MgCl_2$, 6 mM β-mercaptoethanol with 2 units of HaeIII enzyme at 37° C. for two hours, following which 0.1 units of bacterial alkaline phosphatase (type BAPF, Worthington Biochemical Corp., Freehld, N.J., units as defined by manufacturer) were added and digestion continued at 60° C. for ten minutes. Following extraction with one volume of phenol-chloroform, the DNA was precipitated with two volumes of ethanol −70° C., dissolved in 20 μl of 10 mM Tris-HCl, pH 8, 1 mM EDTA, and subjected to electrophoresis on a 6% (w/v) polyacrylamide gel. FIG. 4(F) shows the electrophoresis pattern of the foregoing reaction mixture, which reveals a prominent band corresponding to a nucleotide sequence approximately 550 base-pairs in length. The 550 base-pair fragment was excised from the gel, and eluted electrophoretically, with the result shown in FIG. 4(E).

The remaining material corresponding to the 550 base-pair fragment shown in FIG. 4(E) was digested with 4 units of HhaI endonuclease in 50 μl of the same buffer used for digestion with HaeIII endonuclease, at 37° C. for 2 hours. Following phenol-chloroform extraction and ethanol precipitation, the digestion products were separated by electrophoresis on a 6% (w/v) polyacrylamide gel. The result is shown in FIG. 4(D).

Two fragments were eluted electrophoretically, combined and rejoined by incubation in 20 μl of 66 mM Tris-HCl, pH 7.6, 6 mM $MgCl_2$, 15 mM dithiothreitol, 1 mM ATP containing 20 μg/ml of T4 DNA ligase at 15° C. for two hours. The reaction mixture was then diluted to 200 μl with 0.1 M NaCl, extracted with 1 volume of phenol-chloroform and the DNA precipitated with 2 volumes of ethanol. After resuspension in 20 μl of 10 mM Tris-HCl, pH 8, 1 mM EDTA, the ligation products were separated by electrophoresis in the 6% (w/v) polyacrylamide gel. The result is shown in FIG. 1(C). It can be seen from the electrophoresis pattern of FIG. 4(C) that the 550 nucleotide fragment was reconstituted by the ligation treatment. The prior treatment with alkaline phosphatase insured that the two HhaI fragments were rejoined in the original sequence relative to each other to reconstitute the 550 nucleotide segment. The additional bands seen in FIG. 4(C) were the result of dimer formation between the HhaI fragments, since dimer formation is not prevented by the alkaline phosphatase treatment.

The reconstituted 550 nucleotide fragment was excised from the gel and eluted electrophoretically. The electrophoresis pattern of the eluted material is shown in FIG. 4(B). FIG. 4(A) represents the electrophoresis pattern of $^{32}P$-labeled HaeIII digest of double-stranded M13 DNA used as a size marker. The electrophoretic analyses were conducted in a 6% (w/v) polyacrylamide gel in 50 mM Tris-borate, pH 8, 1 mM EDTA at 100 volts for two hours. Following electrophoresis, the gel was dried and exposed to Kodak NS2T x-ray film to produce the autoradiograms.

PURITY OF RECONSTITUTED 550 NUCLEOTIDE FRAGMENT OF HCS cDNA

The isolated reconstituted HCS cDNA HaeIII fragments was labeled with $^{32}P$ at its 5′ ends using the enzyme polynucleotide kinase obtained from bacteriophage T4-infected *E. Coli* by the method of Panet, A., et al., *Biochemistry* 12, 5045 (1973). Polynucleotide kinase is also commercially available from P-L Biochemical, Milwaukee, Wis. The fragment was then digested with either HhaI or HpaII in 50 μl of 6 mM Tris-Hcl, pH 7.6, 6 mM $MgCl_2$, 6 mM β-mercaptoethanol at 37° C. for two hours. Following extraction with an equal volume of phenol-chloroform, the DNA was precipitated with two volumes of ethanol at −70° C., resuspended in 20 μl, 10 mM Tris-HCl, pH 8, 1 mM EDTA and subjected to electrophoresis, the gel was exposed to x-ray film to visualize the labeled fragments, as described previously.

Figure 5:
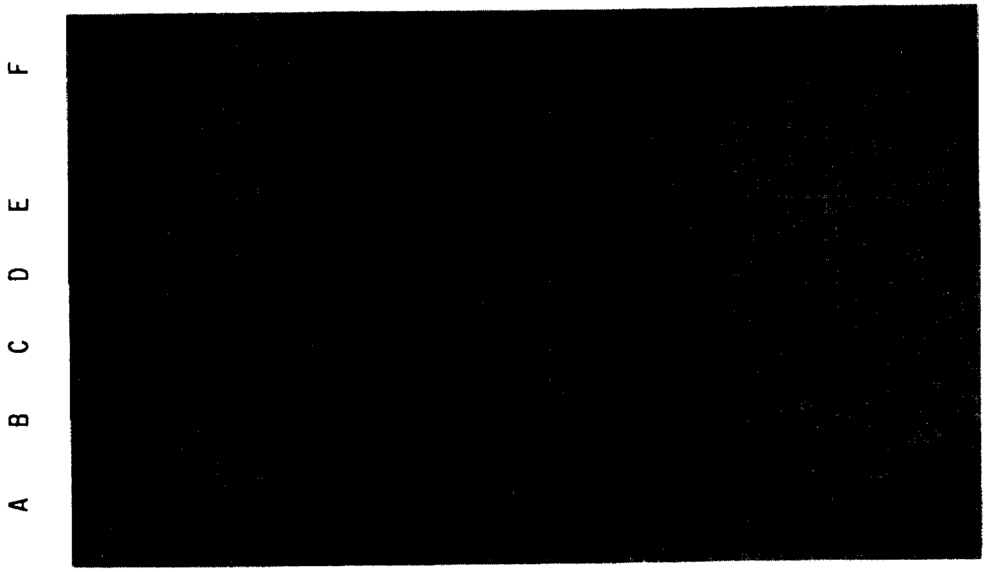
FIGS. 4 and 5 are autoradiograms of gel electrophoresis results using $^{32}P$-labeled cDNA, as described in detail in example 3.

Results are shown in FIG. 5. FIGS. 5(B) and 5(E) represent duplicate runs of the 550 nucleotide fragment prior to restriction enzyme designation. FIG. 5(C) represents the pattern resulting from HhaI cleavage and FIG. 5(D) represents the pattern resulting from HpaII cleavage.

The purity of the 550 nucleotide fragment was measured by scanning the autoradiogram of the restriction enzyme cleavage products and by quantitation of the distribution of radioactivity in each of the two restriction endonuclease digests. Such measurements reveal that the purified humans HCS cDNA reconstituted HaeIII fragment was greater than 99% homogeneous.

EXAMPLE 4

Synthesis of a plasmid containing a nucleotide sequence of 550 base-pairs comprising the majority of the coding region for HCS is described.

A 550 nucleotide fragment of HCS cDNA of greater than 99% purity was prepared as described in example 3. Terminal 5′ phosphate end groups were restored in a reaction mixture containing 50 mM Tris-HCl, pH 8.5, 10 mM $MgCl_2$, 0.1 mM spermidine, 5 mM β-mercaptoethanol, 5% (w/v) glycerol, 333 pmole ATP, 5 units of T4 polynucleotide kinase incubated in a final volume of 40 μl at 37° C. for two hours. DNA was separated from the reaction mixture by phenol extraction followed by ethanol precipitation. Synthetic decanucleotide linkers having restriction site specificity for EcoRI and having the sequence, 5′-CCGAATTCGG-3′, prepared according to Scheller, et al., supra, were then ligated to the HCS DNA in a molar ratio of approximately 50:1 in 50 μl of 66 mM Tris-HCl, pH 7.6, 9 mM $MgCl_2$, 15 mM dithiothreitol, 1 mM ATP and 20 μg/ml T4 DNA ligase. Linkers are commercially available from Collaborative Research, Waltham, Mass. After incubation at 4° C. for 18 hours, the reaction was stopped by extraction with phenol-chloroform. The ligation products were precipitated with ethanol, redissolved in 50 μl 100 mM NaCl, 50 mM Tris-HCl, pH 7.6, 7 mM $MgCl_2$, and digested with 50 units EcoRI endonuclease at 37° C. for 2 hours. Digestion with the endonuclease resulted in cleavage at the EcoRI site of the decamers giving rise to HCS cDNA with EcoRI cohesive ends as well as cleaved unreacted decanucleotides and self-ligated decanucleotides. As the cleaved decamers also contained EcoRI termini and would complete with the HCS cDNA for recombination with the similarly cleaved plasmid, the HCS cDNA was isolated by gel electrophoresis before reaction with the transfer vector. The use of the foregoing decanucleotide linker has the advantage that the HCS cDNA fragment may be reisolated from the plasmid in a form identical to that of the original fragment.

The transfer vector employed was the bacterial plasmid pMB-9, a 3.5×10≠molecular weight molecule containing a single EcoRI site, prepared as described by Rodriguez, R. L., Bolivar, F., Goodman, H. M., Boyer, H. W. and Betlach, M. in *ICN-UCLA Symposium On Molecular and Genetic Biology*, D. P. Wierlich, W. J. Rutter, and C. F. Fox, Eds. (Academic Press, New York, 1976), pp 471–477. The plasmids pMB-9 and pBR-322 (Example 5) are commercially available from Bethesda Research Labs, Rockville, Md. Infection of *E. Coli* with pMB-9 confers resistance to tetracycline. Incorporation of DNA into the EcoRI site of pMB-9 does not affect the tetracycline resistance or any other known property of the plasmid. Consequently, there are no phenotypic differences between recombinant and normal plasmids. Therefore the EcoRI cut pMB-9 was first treated with alkaline phosphatase, according to a method described in detail in application Ser. No. 805,023. See also, Ullrich, et al., supra. Alkaline phosphatase treatment removes the 5′ phosphates from the EcoRI generated ends of the plasmid and prevents self-ligation of the plasmid DNA, insuring that circle formation and hence transformation is dependent on the insertion of a DNA fragment containing 5′ phosphorylated termini. The alkaline phosphatase treatment was carried out in a reaction mixture at the level of 1.0 enzyme units/mg of plasmid DNA in 25 mM Tris-HCl, pH 8, for 30 minutes at 65° C., followed by phenol extraction to remove the phosphatase, and ethanol precipitation of the DNA. Ligation of HCS cDNA to pMB-9 treated as described was carried out in 50 μl reactions containing 60 mM Tris-HCl, pH 8, 10 mM β-mercaptoethanol, 8 mM $MgCl_2$, between 10 and 50 ng of the purified HCS cDNA and approximately 500 ng of EcoRI-cleaved 5' dephosphorylated plasmid DNA. Reactions were begun by addition of T4 DNA ligase to 5 $\mu$g/ml, allowed to proceed at 15° C. for 1 hour and mixture diluted to 0.25 ml with 120 mM NaCl, 1 mM EDTA. The diluted reaction mixture was used directly for transformation of *E. Coli* X-1776.

*E. Coli* X-1776 is a host strain especially developed for recombinant DNA work, certified by NIH as an EK-2 host under the Federal guidelines. The strain is available from Dr. Roy Curtiss III, University of Alabama, Department of Microbiology, Birmingham, Ala. The bacteria were grown in 150 ml of nutrient broth supplemented with 100 $\mu$g/ml diaminopimelic (DAP) and 40 $\mu$g/ml thymine to a cell density of approximately $2\times10^8$ cells/ml. The cells were harvested by centrifugation and washed in 60 ml of 10 mM NaCl, recentrifuged and resuspended in 60 ml of transformation buffer containing 10 mM Tris-HCl, pH 8, 140 mM NaCl, 75 mM $CaCl_2$. The cell suspension was kept on ice for 15 minutes, the cells collected by centrifugation and resuspended in 1.5 ml of the same transformation buffer. The cell suspension, 0.5 ml, was added to 0.25 ml of diluted ligation reaction mixture and incubated on ice for 15 minutes, then transferred to 25° C. for 4 minutes, then on ice again for 30 minutes. The cell suspension, 0.2 ml, was plated directly onto nutrient agar plates supplemented with 100 $\mu$g/ml DAP and 40 $\mu$g/ml thymine and 20 $\mu$g/ml tetracycline. Four transformants were obtained, all of which contained a 550 base-pair insertion which was released from the plasmid DNA by either EcoRI or HaeIII endonuclease digestion.

A transformant clone designated pHCS-1 was selected for sequence analysis. *E. Coli* X-1776—pHCS-1 was grown in suitable nutrient medium, plasmid DNA was isolated therefrom and cleaved with EcoRI endonuclease. The 550 base-pair insertion was isolated from linear pMB-9 by electrophoresis in a 6% polyacrylamide gel and subjected to a DNA sequence analysis using the procedure of Maxam and Gilbert, supra. Subfragments of the HCS DNA were prepared by incubation with HpaII restriction endonuclease and the 5= termini were labeled using $\nu$ $^{32}$P-ATP and polynucleotide kinase. Following the sequence analysis procedure of Maxam and Gilbert, the nucleotide sequence of cloned HCS-DNA was determined. By comparison with the known amino acid sequence of HCS, the 557 nucleotide sequence represented that portion of the coding region of HCS mRNA from amino acids 24 to 191, plus 50 nucleotides of the 3'-untranslated region. See Niall, H. D., Hogan, M. L., Sauer, R., Rosenblum, I. Y. and Greenwood, F. C., *Proc. Nat. Acad. Sci.* USA 68, 866 (1971). The primary structure of HCS mRNA as determined from the DNA sequence of cloned fragment pHCS-1 is shown in Table 3, together with the amino acid sequence predicted therefrom on the basis of the known genetic code. The amino acid sequence determined from the nucleotide sequence is identical with the previously published amino acid sequence determined by chemical means. This demonstrates that the initially isolated HCS mRNA has been copied in vitro with high fidelity and that the cloned HCS DNA fragment was replicated with high fidelity in the transformed bacteria.

TABLE 4

Nucleotide sequence of one strand of HCS DNA from cloned pHCS-1. The numbers refer to the amino acid sequence beginning at the amino terminus. The DNA sequence shown corresponds to the mRNA sequence for HCS, except that U replaces T in the mRNA. The amino acid sequence from positions 1 through 23 is also shown.

1 10 20
Val—Gln—Thr—Val—Pro—Leu—Ser—Arg—Leu—Phe—Asp—His—Ala—Met—Leu—Glu—Ala—His—Arg—Ala—His—Glu—Leu—

24 40
Ala Ile Asp Thr Tyr Gln Glu Phe Glu Glu Thr Tyr Ile Pro Lys Asp Gln Lys Tyr Ser Phe
5'-G GCC ATT GAC ACC TAC CAG GAG TTT GAA GAA ACC TAT ATC CCA AAG GAC CAG AAG TAT TCG TTC

60
Leu His Asp Ser Gln Thr Ser Phe Cys Phe Ser Asp Ser Ile Pro Thr Pro Ser Asn Met Glu Glu
CTG CAT GAC TCC CAG ACC TCC TTC TGC TTC TCA GAC TCT ATT CCG ACA CCC TCC AAC ATG GAG GAA

80
Thr Gln Gln Lys Ser Asn Leu Glu Leu Leu Arg Ile Ser Leu Leu Leu Ile Glu Ser Trp Leu Glu
ACG CAA CAG AAA TCC AAT CTA GAG CTG CTC CGC ATC TCC CTG CTG CTC ATC GAG TCG TGG CTG GAG

100
Pro Val Arg Phe Leu Arg Ser Met Phe Ala Asn Asn Leu Val Tyr Asp Thr Ser Asp Ser Asp Asp
CCC GTC CGG TTC CTC AGG AGT ATG TTC GCC AAC AAC CTG GTG TAT GAC ACC TCG GAC AGC GAT GAC

120
Tyr His Leu Leu Lys Asp Leu Glu Glu Gly Ile Gln Thr Leu Met Gly Arg Leu Glu Asp Gly Ser
TAT CAC CTC CTA AAG GAC CTA GAG GAA CGC ATC CAA ACG CTG ATG GGG AGG CTG GAA GAC GGC AGC

140
Arg Arg Thr Gly Gln Ile Leu Lys Gln Thr Tyr Ser Lys Phe Asp Thr Asn Ser His Asn His Asp
CGC CGG ACT GGG CAG ATC CUC AAG CAG ACC TAC AGC AAG TTT GAC ACA AAC TCG CAC AAC CAT GAC

160
Ala Leu Leu Lys Asn Tyr Gly Leu Leu Tyr Cys Phe Arg Lys Asp Met Asp Lys Val Glu Thr Phe
GCA CTG CTC AAG AAC TAC GGG CTG CUC TAC TGC TTC AGG AAG GAC ATG GAC AAG GTC GAG ACA TTC

180
Leu Arg Met Val Gln Cys Arg Ser Val Glu Gly Ser Cys Gly
CTG CGC ATG GTG CAG TGC CGC TCT GTC GAG GGC AGC TGT GGC

191
Phe

TABLE 4-continued

Nucleotide sequence of one strand of HCS DNA from cloned pHCS-1. The numbers refer to the amino acid sequence beginning at the amino terminus. The DNA sequence shown corresponds to the mRNA sequence for HCS, except that U replaces T in the mRNA. The amino acid sequence from positions 1 through 23 is also shown.

| |
|---|
| TTC TAG GTGCCCGAGTAGCATCCTGTGACCCCTCCCCAGTGCCTCTCCTGGCC -3' |

The generic sequence coding for HCS is $5'\text{-}GTL_1CAJ_2ACL_3GTL_4CCL_5X_6TY_6QR_7S_7W_8GZ_8X_9TY_9TTK_{10}GAK_{11}CAK_{12}GLC_{13}ATG_{14}X_{15}TY_{15}CAJ_{16}GCL_{17}CAK_{18}W_{19}GZ_{19}GCL_{20}CAK_{21}CAJ_{22}X_{23}TY_{23}GCL_{24}ATM_{25}GAK_{26}ACL_{27}TAK_{28}CAJ_{29}GAJ_{30}TTK_{31}GAJ_{32}GAJ_{33}ACL_{34}TAK_{35}ATM_{36}CCL_{37}AAJ_{38}GAK_{39}CAJ_{40}AAJ_{41}TAK_{42}QR_{43}S_{43}TTK_{44}X_{45}TY_{45}CAK_{46}GAK_{47}QR_{48}S_{48}CAJ_{49}ACL_{50}QR_{51}S_{51}TTK_{52}TGK_{53}TTK_{54}QR_{55}S_{55}GAK_{56}QR_{57}S_{57}ATM_{58}CCL_{59}ACL_{60}CCL_{61}QR_{62}S_{62}AAK_{63}ATGGAJ_{65}GAJ_{66}ACL_{67}CAJ_{68}CAJ_{69}AAJ_{70}QR_{71}S_{71}AAK_{72}X_{73}TY_{73}GAJ_{74}X_{75}TY_{75}X_{76}TY_{76}W_{77}GZ_{77}ATM_{78}QR_{79}S_{79}X_{80}TY_{80}X_{81}TY_{81}X_{82}ATM_{83}GAJ_{84}QR_{85}S_{85}TGGX_{87}TY_{87}GAJ_{88}CCL_{89}GTL_{90}W_{91}GZ_{91}TTK_{92}X_{93}TY_{93}W_{94}GZ_{94}QR_{95}S_{95}ATGTTK_{97}GCL_{98}AAK_{99}AAK_{100}X_{101}TY_{101}GTL_{102}TAK_{103}GAK_{104}ACL_{105}QR_{106}S_{106}GAK_{107}QR_{108}S_{108}GAK_{109}GAK_{110}TAK_{111}CAK_{112}X_{113}TY_{113}X_{114}TY_{114}AAJ_{115}GAK_{116}X_{117}TY_{117}GAJ_{118}GAJ_{119}GGL_{120}ATM_{121}CAJ_{122}ACL_{123}X_{124}TY_{124}ATGGGL_{126}W_{127}GZ_{127}X_{128}TY_{128}GAJ_{129}GAK_{130}GGL_{131}QR_{132}S_{132}W_{133}GZ_{133}W_{134}GZ_{134}ACL_{135}GGL_{136}CAJ_{137}ATM_{138}X_{139}TY_{139}AAJ_{140}CAJ_{141}ACL_{142}TAK_{143}QR_{144}S_{144}AAJ_{145}TTK_{146}GAK_{147}ACL_{148}AAK_{149}QR_{150}S_{150}CAK_{151}AAK_{152}CAK_{153}GAK_{154}GCL_{155}X_{156}TY_{156}X_{157}TY_{157}AAJ_{158}AAK_{159}TAK_{160}GGL_{161}X_{162}TY_{162}X_{163}TY_{163}TAK_{164}TGK_{165}TTK_{166}W_{167}GZ_{167}AAJ_{168}GAK_{169}ATGGAK_{171}AAJ_{172}GTL_{173}GAJ_{174}ACL_{175}TTK_{176}X_{177}TY_{177}W_{178}GZ_{178}ATGGTL_{180}CAJ_{181}TGK_{182}W_{183}GZ_{183}QR_{184}S_{184}GTL_{185}GAJ_{186}GGL_{187}QR_{188}S_{188}TGK_{189}GGL_{190}TTK_{191}TAGGTGCCCGAGTAGCATCCTGTGACCCCTCCCCAGTGCCTCTCCTGGCC\text{-}3'$.

EXAMPLE 5

The purification of DNA whose nucleotide sequence comprises most of the coding region for HGH is described, together with the synthesis of a plasmid transfer vector containing the purified DNA and the construction of a microorganism strain having the DNA as part of its genetic makeup. HGH was purified essentially as described for HCS in Example 3, except as noted below.

Five benign human pituitary tumors, quick-frozen in liquid nitrogen after surgical removal, weighing 0.4 g to 1.5 g each were thawed and homogenized in 4 M guanidinium thiocyanate containing 1 M mercaptoethanol buffered to pH 5.0 at 4° C. The homogenate was layered over 1.2 ml 5.7 M CsCl containing 100 mM EDTA and centrifuged for 18 hours at 37,000 rpm in the SW 50.1 rotor of a Beckman ultra-centrifuge at 15° C. (Beckman Instrument Company, Fullerton, Calif.). RNA travelled to the bottom of the tube. Further purification, using an oligo-dT column and sucrose gradient sedimentation was as described previously in Examples 1 and 3. About 10% of the RNA thus isolated coded for growth hormone, as judged by incorporation of a radioactive amino acid precursor into anti-growth hormone precipitable material in a cell-free translation system derived from wheat germ. See Roberts, B. E. and Patterson, B. M., *Proc.Nat.Acad. Sci. USA* 70, 2330 (1973). Single-stranded cDNA and double-stranded cDNA were synthesized as described in Example 3. HGH cDNA was then treated with restriction endonuclease HaeIII and alkaline phosphatase as described in Example 3, then fractionated by gel electrophoresis. A distinct band in a position corresponding to about 550 nucleotides in length was observed, and isolated for further purification.

For further purification, the previously described technique of dividing the DNA into sub-fragments and separately purifying and recombining the sub-fragments was carried out as previously described, except that for HGH, the restriction endonuclease PvuII was used to produce two sub-fragments of approximately 490 and approximately 60 nucleotides length, respectively. All restriction enzymes used herein are commercially available from New England Biolabs, Beverly, Mass. The religated product, about 550 base-pairs in length, was greater than 99% pure as judged by sub-fractionation in four separate restriction endonuclease systems.

Synthesis of a recombinant transfer vector containing HGH DNA was carried out essentially as described in Example 4 except that the decanucleotide linkers and plasmid employed were different. A decanucleotide linker having Hind III specificity was employed, sequence 5'-CCAAGCTTGG-3'. Treatment with HsuI, yielded HGH cDNA with cohesive ends. HsuI and Hind III have the same site specificity and may be used interchangeably. The plasmid pBR-322 was used as the transfer vector. This plasmid confers host resistance to the antibiotics ampicillin and tetracycline. DNA insertions into the Hind III site have been found to reduce or abolish tetracycline resistance. Recombinants were therefore selected by growth on nutrient plates containing ampicillin, and by their inability to grow on 20 μg/ml of tetracycline. HGH-cDNA was recombined with HsuI-cleaved alkaline phosphatase-treated pBR-322, under conditions essentially as described in Example 4.

Products of the ligase reaction were used to transform *E. Coli* X-1776 under conditions as described in Example 4. Seven colonies were isolated based upon their ability to grow in the presence of ampicillin and their inability to grow in the presence of tetracycline. Five of the seven colonies carried the recombinant plasmid containing the approximately 550 base-pair portion of HGH DNA. One of the bacterial strains, pHGH-1, carrying HGH DNA as part of its genetic makeup, was grown in quantity to provide a source of plasmid DNA from which the HGH DNA could be reisolated by treatment with Hind III or HsuI. This isolated HGH DNA, having undergone many replications, was subjected to sequence analysis as described in Example 4. The results are shown in Table 5.

TABLE 5

Nucleotide sequence of one strand of HGH-DNA of cloned pHGH-1. The numbers refer to the amino acid sequence of HGH beginning at the amino terminus. The DNA sequence shown corresponds to the mRNA sequence for HGH, except that U replaces T in the mRNA.

24 34 40 43
Ala Phe Asp Thr Tyr Gln Glu Phe Glu Glu Ala Tyr Ile Pro Lys Glu Gln Lys Tyr Ser Phe
5'-G GCC TTT GAC ACC TAC CAG GAG TTT GAA GAA GCC TAT ATC CCA AAG GAA CAG AAG TAT TCA TTC

60
Leu Gln Asn Pro Gln Thr Ser Leu Cys Phe Ser Glu Ser Ile Pro Thr Pro Ser Asn Asg Glu Glu
CTG CAG AAC CCC CAG ACC TCC CTC TGT TTC TCA GAG TCT ATT CCG ACA CCC TCC AAC AGG GAG GAA

80
Thr Gln Gln Lys Ser Asn Leu Glu Leu Leu Arg Ile Ser Leu Leu Leu Ile Gln Ser Trp Leu Glu
ACA CAA CAG AAA TCC AAC CTA GAG CTG CTC CGC ATC TCC CTG CTG CTC ATC CAG TCG TGG CTG GAG

100
Pro Val Gln Phe Leu Arg Ser Val Phe Ala Asn Asn Leu Val Tyr Gly Ala Ser Asp Ser Asn Val
CCC GTC CAG TTC CTC AGG AGT GTC TTC GCC AAC AAC CTG GTG TAC GGC GCC TCT GAC AGC AAC GTC

120
Tyr Asp Leu Leu Lys Asp Leu Glu Glu Gly Ile Gln Thr Leu Met Gly Arg Leu Glu Asp Gly Ser
TAT GAC CTC CTA AAG GAC CTA GAG GAA GGC ATC CAA ACG CTG ATG GGG AGG CTG GAA GAC GGC AGC

140
Pro Arg Thr Gly Gln Ile Phe Lys Gln Thr Tyr Ser Lys Phe Asp Thr Asn Ser His Asn His Asp
CCC CGG ACT GGG CAG ATC TTC AAG CAG ACC TAC AGC AAG TTC GAC ACA AAC TCA CAC AAC CAT GAC

160
Ala Leu Leu Lys Asn Tyr Gly Leu Leu Tyr Cys Phe Arg Lys Asp Met Asp Lys Val Glu Thr Phe
GCA CTA CTC AAG AAC TAC GGG CTG CTC TAC TGC TTC AGG AAG GAC ATG GAC AAG GTC GAG ACA TTC

180
Leu Arg Ile Val Gln Cys Arg Ser Val Glu Gly Ser Cys Gly
CTG CGC ATC GTG CAG TGC CGC TCT GTG GAG GGC AGC TGT GGC

191
Phe
TTC TAG CTGCCCGGGTGGCATCCCTGTGACCCCTCCCCAGTGCCTCTCCTGGCC -3'

The generic sequence coding for HGH is 5'-$TTK_{1}CCL_{2}ACL_{3}ATM_{4}CCL_{5}X_{6}TY_{6}QR_{7}S_{7}W_{8}GZ_{8}X_{9}TY_{9}TTK_{10}GAK_{11}AAK_{12}GCL_{13}ATGX_{15}TY_{15}W_{16}GZ_{16}GCL_{17}CAK_{18}W_{19}GZ_{19}X_{20}TY_{20}CAK_{21}CAJ_{22}X_{23}TY_{23}GCL_{24}TTK_{25}GAK_{26}ACL_{27}TAK_{28}CAJ_{29}GAJ_{30}TTK_{31}GAJ_{32}GAJ_{33}ACL_{34}TAK_{35}ATM_{36}CCL_{37}AAJ_{38}GAJ_{39}CAJ_{40}AAJ_{41}TAK_{42}QR_{43}S_{43}TTK_{44}X_{45}TY_{45}CAJ_{46}AAK_{47}CCL_{48}CAJ_{49}ACL_{50}QR_{51}S_{51}X_{52}TY_{52}TGK_{53}TTK_{54}QR_{55}S_{55}GAJ_{56}QR_{57}S_{57}ATM_{58}CCL_{59}ACL_{60}CCL_{61}QR_{62}S_{62}AAK_{63}W_{64}GZ_{64}GAJ_{65}GAJ_{66}ACL_{67}CAJ_{68}CAJ_{69}AAJ_{70}QR_{71}S_{71}AAK_{72}X_{73}TY_{73}GAJ_{74}X_{75}TY_{75}X_{76}TY_{76}W_{77}GZ_{77}ATM_{78}QR_{79}S_{79}X_{80}TY_{80}X_{81}TY_{81}X_{82}TY_{82}ATM_{83}CAJ_{84}QR_{85}S_{85}TGGX_{87}TY_{87}GAJ_{88}CCL_{89}GTL_{90}CAJ_{91}TTK_{92}X_{93}TY_{93}W_{94}GZ_{94}QR_{95}S_{95}GTL_{96}TTK_{97}GCL_{98}AAK_{99}AAK_{100}X_{101}TY_{101}GTL_{102}TAK_{103}GGL_{104}GCL_{105}QR_{106}S_{106}GAK_{107}QR_{108}S_{108}AAK_{109}GTL_{110}TAK_{111}GAK_{112}X_{113}TY_{113}X_{114}TY_{114}AAJ_{115}GAK_{116}X_{117}TY_{117}GAJ_{118}GAJ_{119}GGL_{120}ATM_{121}CAJ_{122}ACL_{123}X_{124}TY_{124}ATGGGL_{126}W_{127}GZ_{127}X_{128}TY_{128}GAJ_{129}GAK_{130}GGL_{131}QR_{132}S_{132}CCL_{133}W_{134}GZ_{134}ACL_{135}GGL_{136}CAJ_{137}ATM_{138}TTK_{139}AAJ_{140}CAJ_{141}ACL_{142}TAK_{143}QR_{144}S_{144}AAJ_{145}TTK_{146}GAK_{147}ACL_{148}AAK_{149}QR_{150}S_{150}CAK_{151}AAK_{152}CAK_{153}GAK_{154}GCL_{155}X_{156}TY_{156}X_{157}TY_{157}AAJ_{158}AAK_{159}TAK_{160}GGL_{161}X_{162}TY_{162}X_{163}TY_{163}TAK_{164}TGK_{165}TTK_{166}W_{167}GZ_{167}AAJ_{168}GAK_{169}ATGGAK_{171}AAJ_{172}GTL_{173}GAJ_{174}ACL_{175}TTK_{176}X_{177}TY_{177}W_{178}GZ_{178}ATM_{179}GTL_{180}CAJ_{181}TGK_{182}W_{183}GZ_{183}QR_{184}S_{184}GTL_{185}GAJ_{186}GGL_{187}QR_{188}S_{188}TGK_{189}GGL_{190}TTK_{191}$TAGCTGCCCGGGTGGCATCCCTGTGACCCCTCCCCAGTGCCTCTCCTGGCC-3'.

EXAMPLE 6

The isolation and purification of DNA having the entire structural gene sequence for RGH is described, together with the synthesis of a transfer vector containing the entire structural gene for RGH and the construction of a microorganism strain containing the gene for RGH as part of its genetic makeup.

Where genes of non-human origin are involved, the Federal safety restrictions do not require the isolation of cDNA in such a high degree of purity as that required for human cDNAs. Therefore, it was possible to isolate the cDNA containing the entire RGH structural gene by isolating electrophoretically separated DNA of the expected length, about 800 base-pairs, as determined from the known amino acid length of RGH. Cultured rat pituitary cells, a sub-clone of the cell line GH-1, available from American Type Culture Collection, were used as a source of RGH mRNA. See Tashjian, A. H., et al., *Endochrinology* 82, 342 (1968). In such cells, when grown in normal conditions, growth hormone mRNA represents only a small percentage 1-3% of the total poly-A containing RNA. However, growth hormone mRNA levels were raised above that of other cellular mRNA species by the synergistic action of thyroid hormones and glucocorticoids. RNA was obtained from $5\times10^{8}$ cells grown in suspension culture and induced for growth hormone production by including 1 mM dexamethasone and 10 nM L-triiodothyronine in the medium for 4 days before cell collection. Polyadenylated RNA was isolated from the cytoplasmic membrane fraction of the cultured cells, as described elsewhere. See Martial, J. A., Baxter, J. D., Goodman, H. M. and Seeburg, P. H., *Proc.Nat.Acad.Sci. USA* 74, 1816 (1977), and Bancroft, F. C., Wu, G. and Zubay, G., *Proc.Nat.Acad. Sci. USA* 70, 3646 (1973). The mRNA was further purified and transcribed into double-stranded cDNA essentially as described in examples 1 and 3, supra. Upon fractionation by gel electrophoresis, a faint but distinct band corresponding to a DNA of about 800 base-pairs length was observed.

Treatment of total cDNA transcribed from the cultured pituitary cell mRNA with HhaI endonuclease yielded two major DNA fragments upon electrophoretic separation corresponding to approximately 320 nucleotides (fragment A) and 240 nucleotides (fragment B). Nucleotide sequence analysis of fragments A and B as described in example 4, revealed that these fragments were in fact portions of the coding region for RGH, based on published RGH amino acid sequence data and by comparison with other known growth hormone sequences. See Wallis, M. and Davies, R. V. N., *Growth Hormone And Related Peptides* (Eds., Copecile, A., and Muller, E. E.), pp 1-14 (Elsevier, N.Y., 1976), and Dayhoff, M. O., *Atlas of Protein Sequence and Structure,* 5, suppl. 2, pp 120-121 (National Biomedical Research Foundation, Wash., D.C., 1976). When the 800 base-pair double-stranded cDNA isolated electrophoretically as described, supra, was similarly subjected to HhaI endonuclease treatment, two fragments corresponding in length to fragments A and B were found among the major cleavage products.

Since the approximately 800 base-pair RGH-cDNA was not purified by resort to restriction endonuclease treatment, it was necessary to treat the DNA in order to remove any unpaired single-strand ends. In practice, treatment to remove such unpaired ends was carried out prior to electrophoretic separation in 25 μl of 60 mM Tris-HCl, pH 7.5, 8 mM $MgCl_2$, 10 mM β-mercaptoethanol, 1 mM ATP and 200 μM each of dATP, dTTP, dGTP and dCTP. The mixture was incubated with 1 unit of *E. Coli* DNA polymerase I at 10° C. for 10 minutes to exonucleolytically remove any 3′ protruding ends and to fill any 5′ protruding ends. DNA polymerase I is commercially available from Boehringer-Mannheim Biochemicals, Indianapolis, Ind.

The approximately 800 base-pair RGH-cDNA was treated by the addition of chemically synthesized Hind III linkers, as described in Example 4. The plasmid pBR-322, pretreated with Hind III endonuclease and alkaline phosphatase, as described in Example 5, was combined with the 800 base-pair RGH-cDNA in a DNA ligase reaction mixture as described in Example 4.

The ligase reaction mixture was used to transform a suspension of *E. Coli* X-1776 cells, treated as previously described in Example 4. Recombinant colonies were selected as described in Example 5. Ten such colonies were obtained all of which carried plasmid with an insert of approximately 800 base-pairs that was released by Hind III cleavage.

The 800 base-pair RGH-DNA was isolated in preparative amounts from recombinant clone pRGH-1 and its nucleotide sequence determined as described in Example 4. In this instance, the nucleotide sequence included portions of the 5′ untranslated region of RGH, as well as a 26 amino acid sequence found in the growth hormone precursor protein prior to secretion. The messenger of the mRNA sequence deduced from the gene sequence is shown in Table 5. The predicted amino acid sequence is in good agreement, except in positions 1 and 8, with the partial amino acid sequence of rat growth hormone as described by Wallis and Davies, supra, which comprises residues 1-43, 65-69, 108-113, 133-143 and 150-190.

EXAMPLE 7

The isolation and purification of the entire gene sequence coding for HGH is described, together with the synthesis of a recombinant plasmid containing the entire structural gene for HGH, and the production of a microorganism having the entire structural gene for HGH as part of its genetic makeup is described.

The isolation of HGH mRNA is carried out essentially as described in Example 6, except that the biological source material is human pituitary tumor tissue, essentially as described in Example 5. Preparation of HGH-cDNA is carried out essentially as described in Example 6. The HGH-cDNA is fractionated by gel electrophoresis and material migrating to a position corresponding to about 800 nucleotides in length is selected for cloning. The selected fraction is treated with DNA polymerase I as described in Example 6, then treated by the end addition of Hind III linkers. The cDNA is then recombined with alkaline phosphatase-treated plasmid pBR-322 using DNA ligase. *E. Coli* X-1776 is transformed with the recombinant DNA and a strain containing HGH DNA is selected. The HG-DNA containing strain is grown in preparative amounts, the HGH-DNA isolated therefrom and the nucleotide sequence thereof determined. The cloned HGH DNA is found to comprise nucleotides coding for the entire amino acid sequence of HGH. The first twenty-three amino acids of HGH are 10 20
$H_2$—Phe—Pro—Thr—Ile—Pro—Leu—Ser—Arg—Leu—Phe—Asp—Asn—Ala—Met—Leu—Arg—Ala—His—Arg—Leu—His—Gln—Leu—.

The remainder of the sequence is shown in Table 6.

TABLE 6

DNA nucleotide sequence of one strand, containing entire sequence coding for RGH. Corresponding amino acids are shown, together with their position number relative to the amino terminus. Negatively numbered amino acids represent the pre-growth hormone sequence. The corresponding mRNA sequence is the same, except that U represents T in the mRNA.

5′-GTGGACAGATCACTGAGTGGCG

-26
Met Ala Ala Asp Ser Gln Thr Pro Trp Leu Leu Thr Phe Ser Leu Leu Cys Leu Leu Trp Pro
ATG GCT GCA GAC TCT CAG ACT CCC TGG CTC CTG ACC TTC AGC CTG CTC TGC CTG CTG TGG CCT

1
Gln Glu Ala Gly Ala Leu Pro Ala Met Pro Leu Ser Ser Leu Phe Ala Asn Ala Val Leu Arg
CAA GAG GCT GGT GCT TTA CCT GCC ATG CCC TTG TCC AGT CUG TTT GCC AAT GCT GTG CTC CGA

TABLE 6-continued

DNA nucleotide sequence of one strand, containing entire sequence coding for RGH. Corresponding amino acids are shown, together with their position number relative to the amino terminus. Negatively numbered amino acids represent the pre-growth hormone sequence. The corresponding mRNA sequence is the same, except that U represents T in the mRNA.

20
Ala Gln His Leu His Gln Leu Ala Ala Asp Thr Tyr Lys Glu Phe Glu Arg Ala Tyr Ile Pro
GCC CAG CAC CTG CAC CAG CTG GCT GCT GAC ACC TAC AAA GAG TTC GAG CGT GCC TAC ATT CCC

40
Glu Gly Gln Arg Tyr Ser Ile Gln Asn Ala Gln Ala Ala Phe Cys Phe Ser Glu Thr Ile Pro
GAG GGA CAG CGC TAT TCC ATT CAG AAT GCC CAG GCT GCT TTC TGC TTC TCA CAG ACC ATC CCA

60
Ala Pro Thr Gly Lys Glu Glu Ala Gln Gln Arg Thr Asp Met Glu Leu Leu Arg Phe Ser Leu
GCC CCC ACC GGC AAG GAG GAG GCC CAG CAG AGA ACT GAC ATG GAA TTG CTT CGC TTC TCG CTG 80 100
Leu Leu Ile Gln Ser Trp Leu Gly Pro Val Gln Phe Leu Ser Arg Ile Phe Thr Asn Ser Leu
CTG CTC ATC CAG TCA TGG CTG GGG CCC GTG CAG TTT CTC AGC AGG ATG TTT ACC AAC AGC CTG

120
Met Phe Gly Thr Ser Asp Arg Val Tyr Glu Lys Leu Lys Asp Leu Glu Glu Gly Ile Gln Ala
ATG TTT GGT ACC TCG GAC CGC GTC TAT GAG AAA CTG AAG GAC CTG GAA GAG GGC ATC CAG GCT

140
Leu Met Gln Glu Leu Glu Asp Gly Ser Pro Arg Ile Gly Gln Ile Leu Lys Gln Thr Tyr Asp
CTG ATG CAG GAG CTG GAA GAC GGC AGC CCC CGT ATT CGG CAG ATC CTC AAG CAA ACC TAT GAC

160
Lys Phe Asp Ala Asn Met Arg Ser Asp Asp Ala Leu Leu Lys Asn Tyr Gly Leu Leu Ser Cys
AAG TTT GAC GCC AAC ATG CGC AGC GAT GAC GCT CTG CTC AAA AAC TAT GGG CTG CTC TCC TGC

180
Phe Lys Lys Asp Leu His Lys Ala Glu Thr Tyr Leu Arg Val Met Lys Cys Arg Arg Phe Ala
TTC AAG AAG GAC CTG CAC AAG GCA GAG ACC TAC CTG CGG GTC ATG AAG TGT CGC CGC TTT GCG

Glu Ser Ser Cys Ala Phe
GAA AGC AGC TGT GCT TTC TAG GCACACACTGGTGTCTCTGCGGCACTCCCCCGTTACCCCCCTGTACTCGG
CAACTGCCACCCCTACACTTTGTCCTAATAAAATTAATGATGCATCATATC poly(A) -3'

GENERAL CONCLUDING REMARKS

The process of the present invention provides for the first time a method of general applicability for purifying desired specific nucleotide sequences. These sequences may be correlated with the production of a specific protein of commercial or medical significance. The disclosed process results in the purification of nucleotide sequences which may be fragments of a larger sequence coding for the desired protein. The present method may be used in combination with known ancillary procedures to produce the entire nucleotide sequence coding for a specific protein.

In addition, a method has been disclosed whereby a nucleotide sequence of specific length, however derived, may be highly purified. A method for measuring the degree of purity of such fragments is also disclosed. By these means, a nucleotide sequence coding for a portion of human HCS has been isolated, purified and shown to be at least 99% pure.

Transfer vectors containing most of the nucleotide sequence coding for HCS, most of the sequence coding for HGH and all of the sequence coding for RGH, respectively have been synthesized. Novel microorganism strains containing the foregoing genes and portions of genes have been produced. The foregoing nucleotide sequences have been reisolated after many cycles of replication in the host microorganism and found to contain essentially the identical nucleotide sequence to that existing in the source organism. The techniques disclosed herein for isolation, purification and identification of a desired specific nucleotide sequence make it possible to synthesize transfer vectors, and develop microorganism strains, containing the structural gene for the growth hormone of any animal species including man.

On the basis of the genetic code, there exists a finite set of nucleotide sequences which can genetically code for a given amino acid sequence. All such equivalent nucleotide sequences are operable variants of the disclosed sequences, since all give rise to the same protein hormone, having the same amino acid sequence, during the course of in vivo transcription and translation. Consequently, all such variants are included in the scope of the present invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The recombinant plasmids described herein, pHGH-1, pRGH-1 and pHCS-1 were deposited April 3, 1978 in the American Type Culture Collection, 12301 Parklawn Drive, Rockville, Md. 20852, and have been assigned the ATCC accession numbers 40,000, 40,001 and 40,002, respectively.

What is claimed is:

1. A recombinant DNA transfer vector comprising codons for human chorionic somatomammotropin comprising the nucleotide sequence:

5'-G $GCL_{24}ATM_{25}GAK_{26}ACL_{27}TAK_{28}CAJ_{29}GAJ_{30}TTK_{31}GAJ_{32}GAJ_{33}ACL_{34}$.

TAK$_{35}$ATM$_{36}$CCL$_{37}$AAJ$_{38}$GAK$_{39}$CAJ$_{40}$AAJ$_{41}$TAK$_{42}$QR$_{43}$S$_{43}$TTK$_{44}$X$_{45}$TY$_{45}$CAK$_{46}$GAK$_{47}$QR$_{48}$S$_{48}$CAJ$_{49}$ACL$_{50}$QR$_{51}$S$_{51}$TTK$_{52}$TGK$_{53}$TTK$_{54}$QR$_{55}$S$_{55}$GAK$_{56}$QR$_{57}$S$_{57}$ATM$_{58}$CCL$_{59}$ACL$_{60}$CCL$_{61}$QR$_{62}$S$_{62}$AAK$_{63}$ATGGAJ$_{65}$GAJ$_{66}$ACL$_{67}$CAJ$_{68}$CAJ$_{69}$AAJ$_{70}$QR$_{71}$S$_{71}$AAK$_{72}$X$_{73}$TY$_{73}$GAJ$_{74}$X$_{75}$TY$_{75}$X$_{76}$TY$_{76}$W$_{77}$GZ$_{77}$ATM$_{78}$QR$_{79}$S$_{79}$X$_{80}$TY$_{80}$X$_{81}$TY$_{81}$X$_{82}$TY$_{82}$ATM$_{83}$GAJ$_{84}$QR$_{85}$S$_{85}$TGGX$_{87}$TY$_{87}$GAJ$_{88}$CCL$_{89}$GTL$_{90}$W$_{91}$GZ$_{91}$TTK$_{92}$X$_{93}$TY$_{93}$W$_{94}$GZ$_{94}$QR$_{95}$S$_{95}$ATGTTK$_{97}$GCL$_{98}$AAK$_{99}$AAK$_{100}$X$_{101}$TY$_{101}$GTL$_{102}$TAK$_{103}$GAK$_{104}$ACL$_{105}$QR$_{106}$S$_{106}$GAK$_{107}$QR$_{108}$S$_{108}$GAK$_{109}$GAK$_{110}$TAK$_{111}$CAK$_{112}$X$_{113}$TY$_{113}$X$_{114}$TY$_{114}$AAJ$_{115}$GAK$_{116}$X$_{117}$TY$_{117}$GAJ$_{118}$GAJ$_{119}$GGL$_{120}$ATM$_{121}$CAJ$_{122}$ACL$_{123}$X$_{124}$TY$_{124}$ATGGGL$_{126}$W$_{127}$GZ$_{127}$X$_{128}$TY$_{128}$GAJ$_{129}$GAK$_{130}$GGL$_{131}$QR$_{132}$S$_{132}$W$_{133}$GZ$_{133}$W$_{134}$GZ$_{134}$ACL$_{135}$GGL$_{136}$CAJ$_{137}$ATM$_{138}$X$_{139}$TY$_{139}$AAJ$_{140}$CAJ$_{141}$ACL$_{142}$TAK$_{143}$QR$_{144}$S$_{144}$AAJ$_{145}$TTK$_{146}$GAK$_{147}$ACL$_{148}$AAK$_{149}$QR$_{150}$S$_{150}$CAK$_{151}$AAK$_{152}$CAK$_{153}$GAK$_{154}$GCL$_{155}$X$_{156}$TY$_{156}$X$_{157}$TY$_{157}$AAJ$_{158}$AAK$_{159}$TAK$_{160}$GGL$_{161}$X$_{162}$TY$_{162}$X$_{163}$TY$_{163}$TAK$_{164}$TGK$_{165}$TTK$_{166}$W$_{167}$GZ$_{167}$AAJ$_{168}$GAK$_{169}$ATGGAK$_{171}$AAJ$_{172}$GTL$_{173}$GAJ$_{174}$ACL$_{175}$TTK$_{176}$X$_{177}$TY$_{177}$W$_{178}$GZ$_{178}$ATGGTL$_{180}$CAJ$_{181}$TGK$_{182}$W$_{183}$GZ$_{183}$QR$_{184}$S$_{184}$GTL$_{185}$GAJ$_{186}$GGL$_{187}$QR$_{188}$S$_{188}$TGK$_{189}$GGL$_{190}$TTK$_{191}$TAGGTGCCCGAGTAGCATCCTGTGACCCCTCCCCAGTGCCTCTCCTGGCC-3' wherein A is deoxyadenyl,
G is deoxyguanyl,
C is deoxycytosyl,
T is thymidyl,
J is A or G;
K is T or C;
L is A,T,C or G;
M is A, C or T;
X is T or C, if the succeeding Y is A or G, and C if the succeeding Y is C or T;
Y is A, G, C or T, if the preceding X is C, and A or G if the preceding X is T;
W is C or A, if the succeeding Z is G or A, and C if the succeeding Z is C or T;
Z is A, G, C or T, if the preceding W is C, and A or G if the preceding W is A;
QR is TC, if the succeeding S is A, G, C or T, and AG if the succeeding S is T or C;
S is A, G, C or T, if the preceding QR is TC, and T or C if the preceding QR is AG and subscript numerals refer to the amino acid position in human growth hormone, for which the nucleotide sequence corresponds, according to the genetic code, the amino acid positions being numbered from the amino end.

2. The recombinant DNA transfer vector of claim 1 wherein

J is A in amino acid positions: 32, 33, 66, 68, 70, 119, 122 and 129,
J is G in amino acid positions: 29, 30, 38, 40, 41, 49, 65, 69, 74, 84, 88, 115, 118, 137, 140, 141, 145, 158, 168, 172, 174, 181 and 186;
K is T in amino acid positions: 31, 35, 42, 46, 72, 103, 109, 111, 146, 153 and 189;
K is C in amino acid positions: 26, 28, 39, 44, 47, 52, 53, 54, 56, 63, 92, 97, 99, 100, 104, 107, 110, 112, 116, 130, 143, 147, 149, 151, 152, 154, 159, 160, 164, 165, 166, 169, 171, 176, 182 and 191;
L is A in amino acid positions: 37, 60, 148, 155 and 175;
L is T in amino acid position: 135;
L is G in amino acid positions: 59, 67, 90, 102, 123, 126, 136, 161, 180 and 185;
L is C in amino acid positions: 24, 27, 34, 50, 61, 89, 98, 105, 120, 131, 142, 173, 187 and 190;
M is T in amino acid positions: 25 and 58;
M is C in amino acid positions: 36, 78, 83, 121 and 138;
X is C;
Y is A in amino acid positions: 73, 114 and 117;
Y is G in amino acid positions: 45, 75, 80, 81, 87, 101, 124, 128, 156, 162 and 177;
Y is C in amino acid positions: 76, 82, 93, 113, 139, 157 and 163;
W is A in amino acid positions: 94, 127 and 167;
W is C in amino acid positions: 77, 91, 133, 134, 178 and 183;
Z is G in amino acid positions: 91, 94, 127, 134 and 167;
Z is C in amino acid positions: 77, 133, 178 and 183;
QR is AG in amino acid positions: 95, 108, 132, 144 and 188;
QR is TC in amino acid positions: 43, 48, 51, 55, 57, 62, 71, 79, 85, 106, 150 and 184;
S is A in amino acid position: 55;
S is T in amino acid positions: 57, 95 and 184;
S is G in amino acid positions: 43, 85, 106 and 150; and
S is C in amino acid positions: 48, 51, 62, 71, 79, 108, 132, 144 and 188.

3. A recombinant DNA transfer vector according to claim 1 comprising in the nucleotide sequence, 5'-GTL$_{1}$CAJ$_{2}$ACL$_{3}$GTL$_{4}$CCL$_{5}$X$_{6}$TY$_{6}$QR$_{7}$S$_{7}$W$_{8}$GZ$_{8}$X$_{9}$TY$_{9}$TTK$_{10}$GAK$_{11}$CAK$_{12}$GCL$_{13}$ATGX$_{15}$TY$_{15}$CAJ$_{16}$GCL$_{17}$CAK$_{18}$W$_{19}$GZ$_{19}$GCL$_{20}$CAK$_{21}$CAJ$_{22}$X$_{23}$TY$_{23}$ wherein Y$_{23}$ is followed by GCL$_{24}$ in the sequence of claim 15.

4. A recombinant plasmid vector comprising the nucleotide sequence coding for the growth hormone of an animal species and capable of transforming a microorganism, synthesized by a process comprising:

isolating polyadenylated RNA from pituitary cells of the animal species,
preparing double-stranded cDNA transcripts of the isolated RNA,
fractionating the cDNA according to its molecular length, in order to produce a fraction enriched for cDNA coding for the growth hormone of the animal species,
joining the cDNA coding for growth hormone covalently with a plasmid vector to produce a recombinant plasmid capable of transforming a microorganism.

5. A recombinant DNA transfer vector according to claim 2 wherein the transfer vector comprises the plasmid pMB-9.

6. A recombinant DNA transfer vector comprising codons for human growth hormone, comprising the nucleotide sequence:

5'-G GCL$_{24}$TTK$_{25}$GAK$_{26}$ACL$_{27}$TAK$_{28}$CAJ$_{29}$GAJ$_{30}$TTK$_{31}$GAJ$_{32}$GAJ$_{33}$ACL$_{34}$TAK$_{35}$ATM$_{36}$CCL$_{37}$AAJ$_{38}$GAJ$_{39}$CAJ$_{40}$AAJ$_{41}$TAK$_{42}$QR$_{43}$S$_{43}$TTK$_{44}$X$_{45}$TY$_{45}$CAJ$_{46}$AAK$_{47}$CCL$_{48}$CAJ$_{49}$ACL$_{50}$QR$_{51}$S$_{51}$X$_{52}$TY$_{52}$TGK$_{53}$TTK$_{54}$QR$_{55}$S$_{55}$GAJ$_{56}$QR$_{57}$S$_{57}$ATM$_{58}$CCL$_{59}$ACL$_{60}$CCL$_{61}$QR$_{62}$S$_{62}$AAK$_{63}$W$_{64}$GZ$_{64}$GAJ$_{65}$GAJ$_{66}$AC- $L_{67}CAJ_{68}CAJ_{69}AAJ_{70}QR_{71}S_{71}AAK_{72}X_{73}TY_{73}GAJ_{74}X_{75}TY_{75}X_{76}TY_{76}W_{77}GZ_{77}ATM_{78}QR_{79}S_{79}X_{80}TY_{80}X_{81}TY_{81}X_{82}TY_{82}ATM_{83}CAJ_{84}QR_{85}S_{85}TGGX_{87}TY_{87}GAJ_{88}CCL_{89}GTL_{90}CAJ_{91}TTK_{92}X_{93}TY_{93}W_{94}GZ_{94}QR_{95}S_{95}GTL_{96}TTK_{97}GCL_{98}AAK_{99}AAK_{100}X_{101}TY_{101}GTL_{102}TAK_{103}GGL_{104}GCL_{105}QR_{106}S_{106}GAK_{107}QR_{108}S_{108}AAK_{109}GTL_{110}TAK_{111}GAK_{112}X_{113}TY_{113}X_{114}TY_{114}AAJ_{115}GAK_{116}X_{117}TY_{117}GAJ_{118}GAJ_{119}GGL_{120}ATM_{121}CAJ_{122}ACL_{123}X_{124}TY_{124}ATGGGL_{126}W_{127}GZ_{127}X_{128}TY_{128}GAJ_{129}GAK_{130}$ $GGL_{131}QR_{132}S_{132}CCL_{133}W_{134}GZ_{134}ACL_{135}GGL_{136}CAJ_{137}ATM_{138}TTK_{139}AAJ_{140}CAJ_{141}ACL_{142}TAK_{143}QR_{144}S_{144}AAJ_{145}TTK_{146}GAK_{147}ACL_{148}AAK_{149}QR_{150}S_{150}CAK_{151}AAK_{152}CAK_{153}GAK_{154}GCL_{155}X_{156}TY_{156}X_{157}TY_{157}AAJ_{158}AAK_{159}TAK_{160}GGL_{161}X_{162}TY_{162}X_{163}TY_{163}TAK_{164}TGK_{165}TTK_{166}W_{167}GZ_{167}AAJ_{168}GAK_{169}ATGGAK_{171}AAJ_{172}GTL_{173}GAJ_{174}ACL_{175}TTK_{176}X_{177}TY_{177}W_{178}GZ_{178}ATM_{179}GTL_{180}CAJ_{181}TGK_{182}W_{183}GZ_{183}QR_{184}S_{184}GTL_{185}GAJ_{186}GGL_{187}QR_{188}S_{188}TGK_{189}GGL_{190}TTK_{191}$TAGCTGCCCGGGTGGCATCCCTGTGACCCCTCCCCAGTGCCTCTCCTGGCC-3' wherein A is deoxyadenyl,
G is deoxyguanyl,
C is deoxycytosyl,
T is thymidyl,
J is A or G;
K is T or C;
L is A,T,C or G;
M is A, C or T;
X is T or C, if the succeeding Y is A or G, and C if the succeeding Y is C or T;
Y is A, G, C or T, if the preceeding X is C, and A or G if the preceding X is T;
W is C or A, if the succeeding Z is G or A, and C if the succeeding Z is C or T;
Z is A, G, C or T, if the preceding W is C, and A or G if the preceding W is A;
QR is TC, if the succeeding S is A, G, C or T, and AG if the succeeding S is T or C;
S is A, G, C or T, if the preceding QR is TC, and T or C is the preceding QR is AG and subscript numerals refer to the amino acid position in human growth hormone, for which the nucleotide sequence corresponds, according to the genetic code, the amino acid positions being numbered from the amino end.

7. The recombinant DNA transfer vector of claim 6 wherein

J is A in amino acid positions: 32, 33, 39, 66, 68, 70, 119, 122 and 129,
J is G in amino acid positions: 29, 30, 38, 40, 41, 46, 49, 56, 65, 69, 74, 84, 88, 91, 115, 118, 137, 140, 141, 145, 158, 168, 172, 174, 181 and 186;
K is T in amino acid positions: 25, 31, 35, 42, 53, 111, 153 and 189;
K is C in amino acid positions: 26, 28, 44, 47, 54, 63, 72, 92, 97, 99, 100, 103, 107, 109, 112, 116, 130, 139, 143, 146, 147, 149, 151, 152, 154, 159, 160, 164, 165, 166, 169, 171, 176, 182 and 191;
L is A in amino acid positions: 37, 60, 67, 148, 155 and 175;
L is T in amino acid position: 135;
L is G in amino acid positions: 59, 90, 102, 123, 126, 136, 161, 180 and 185;
L is C in amino acid positions: 24, 27, 34, 48, 50, 61, 89, 96, 98, 104, 105, 110, 120, 131, 133, 142, 173, 187 and 190;
M is T in amino acid position: 58;
M is C in amino acid positions: 36, 78, 83, 121, 138, and 179;
X is C;
Y is A in amino acid positions: 73, 114, 117 and 156;
Y is G in amino acid positions: 45, 75, 80, 81, 87, 101, 124, 128, 162 and 177;
Y is C in amino acid positions: 52, 76, 82, 93, 113, 157 and 163;
W is A in amino acid positions: 64, 94, 127 and 167;
W is C in amino acid positions: 77, 134, 178 and 183;
Z is G in amino acid positions: 64, 94, 127, 134 and 167;
Z is C in amino acid positions: 77, 178 and 183;
QR is AG in amino acid positions: 95, 108, 132, 144 and 188;
QR is TC in amino acid positions: 43, 51, 55, 57, 62, 71, 79, 85, 106, 150 and 184;
S is A in amino acid positions: 43, 55 and 150;
S is T in amino acid positions: 57, 95, 106 and 184;
S is G in amino acid position: 85, and
S is C in amino acid positions: 51, 62, 71, 79, 108, 132, 144 and 188.

8. A transfer vector according to claim 7 comprising in addition the nucleotide sequence, 5'-$TTK_{1}CCL_{2}ACL_{3}ATM_{4}CCL_{5}X_{6}TY_{6}QR_{7}S_{7}W_{8}GZ_{8}X_{9}TY_{9}TTK_{10}GAK_{11}AAK_{12}GCL_{13}ATGX_{15}TY_{15}W_{16}GZ_{16}GCL_{17}CAK_{18}W_{19}GZ_{19}X_{20}TY_{20}CAK_{21}CAJ_{22}X_{23}TY_{23}$-3' and wherein $Y_{23}$ is followed in sequence by $GCL_{24}$ in the sequence of claim 6.

* * * * *